(12) United States Patent
Miyakawa et al.

(10) Patent No.: US 6,777,427 B2
(45) Date of Patent: Aug. 17, 2004

(54) TETRAHYDROQUINOLINE COMPOUNDS

(75) Inventors: Motonori Miyakawa, Kyoto (JP); Seiji Amano, Kyoto (JP); Misa Kamei, Kyoto (JP); Keigo Hanada, Kyoto (JP); Kazuyuki Furuya, Kyoto (JP); Noriko Yamamoto, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/380,589

(22) PCT Filed: Sep. 14, 2001

(86) PCT No.: PCT/JP01/07991

§ 371 (c)(1),
(2), (4) Date: Mar. 13, 2003

(87) PCT Pub. No.: WO02/22585

PCT Pub. Date: Mar. 21, 2002

(65) Prior Publication Data

US 2003/0216428 A1 Nov. 20, 2003

(30) Foreign Application Priority Data

Sep. 14, 2000 (JP) ........................................ 2000-279180

(51) Int. Cl.[7] ...................... A61K 31/47; C07D 215/16; C07D 215/14; C07D 215/00; C07D 215/18
(52) U.S. Cl. ........................ 514/311; 514/312; 514/313; 514/314; 546/153; 546/155; 546/156; 546/159; 546/164; 546/168; 546/169; 546/170; 546/171; 546/174; 546/175; 546/176; 546/177; 546/178; 546/180
(58) Field of Search ................................ 546/153, 155, 546/156, 159, 164, 168, 169, 170, 171, 174, 175, 176, 177, 178, 179, 180; 514/311, 312, 313, 314

(56) References Cited

U.S. PATENT DOCUMENTS 5,696,133 A * 12/1997 Jones et al. .................. 546/153

FOREIGN PATENT DOCUMENTS

| EP | 0385271 A1 | 9/1990 |
|----|------------|--------|
| EP | 0987251 A1 | 3/2000 |
| GB | 2069498 A | 8/1981 |
| WO | WO 96/19458 | 6/1996 |
| WO | WO 00/17164 | 3/2000 |

OTHER PUBLICATIONS

Katritzky, A. (1999), J. Heterocycl. Chem., No. 3, 36:755–759.
Park, K. (1995), Tetrahedron Lett., No. 33, 36:5943–6.
Katritzky, A. (1995), J. Organic Chem., No. 13, 60:3993–4001.
Crabb, T. (1994), J. Chemical Society, Perkin Trans., 1:9–13.
Narasaka, K. (1993), Heterocycles, No. 2, 35:1039–53.
Clerici, A. (1990), Tetrahedron Lett., No. 14, 31:2069–72.
Forrest, T.P. (1985), Can. J. Chemical, No. 2, 63:412–17.
Dauphinee, G.A. (1978), Can. J. Chemical, No. 5, 56:632–4.
Zh. Strukt. Khim. (1975), No. 2, 16:237–41.
Zh. Obshch. Khim. (1974), No. 10, 44:2305–6.
Forrest, T.P. (1974), Can. J. Chemical, No. 6, 52:884–7.
Chemical Abstracts, (1963), 59:9973b.
Scindler, V.O. (1979), Helv. Chim. Acta., No. 4, 53:776–779.

* cited by examiner

Primary Examiner—Joseph Mckane
Assistant Examiner—Raymond Covington
(74) Attorney, Agent, or Firm—Nixon Peabody LLP

(57) ABSTRACT

Tetrahydroquinoline compounds of general formula (I) or pharmacologically acceptable salts thereof, which have a specific and strong binding affinity for AR, exhibit AR agonism or antagonism, have therapeutic effects on AR-mediated diseases, particularly by not acting excessively on the prostate as AR agonists, but by showing potent action on skeletal muscle tissue and bone tissue; and pharmaceutical compositions comprising the compounds or the salts as active ingredients:

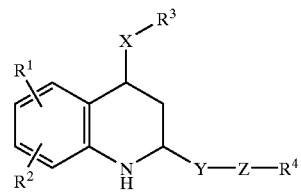

3 Claims, No Drawings

TETRAHYDROQUINOLINE COMPOUNDS

TECHNICAL FIELD

This invention relates to tetrahydroquinoline compounds or pharmacologically acceptable salts thereof which have a specific and strong binding affinity for androgen receptors and exhibit androgen receptor agonism or antagonism, and pharmaceutical compositions containing the compounds or their pharmacologically acceptable salts.

BACKGROUND ART

Androgens are a generic name for C19 steroids. They are sex hormones important for the normal sexual differentiation and growth of males, masculinization at puberty, activation of initial spermatogenesis in the testes, and maintenance of male function. About 90% of androgens are produced by Leydig cells of the testes, the remaining 10% by the adrenal gland, mainly as testosterone, and secreted into the blood. Testosterone is taken up into target cells, and converted by 5α-reductase into dihydrotestosterone (DHT) with potent biological activity. DHT, as well as testosterone, plays an important role in the development of male secondary sex characteristics (growth of sebaceous glands, acne, development of body hair, voice deepening, development of beards), growth of external genitalia (penis, testis), growth of sex accessory organs (prostate, seminal vesicles), sexual stimuli, and occurrence of erection.

In addition to these major actions, androgens have actions other than those on the reproductive system, such as protein anabolic action (increases in skeletal muscles and bone mass), suppression of gonadotropin secretion, and acceleration of erythropoiesis promoting action. Target cells for androgens are localized in external and sex accessory tissues, and are widely distributed in the brain, pituitary gland, muscular tissues, bones, and kidneys (N. Engl. J. Med. 334, 707–714, 1996).

In addition to these roles, androgens are reported to show an anti-inflammatory action. Nowadays, it is becoming clear that androgens attenuate arthritis and autoimmune disease by inhibiting the proliferation of inflammatory cells or suppressing the production of cytokines such as IL-6 (Ann. Rheum. Dis. 55, 811–815, 1996).

All androgenic actions are mediated through androgen receptor (hereinafter referred to as AR) having a molecular weight of about 100,000 which is present in the nuclei of target cells. The gene of AR was cloned by Chang and Lubahn et al. in 1988. Their study demonstrated that AR has a similar structure to estrogen, progesterone, mineral corticoid, and glucocorticoid receptors, and they build a nuclear steroid receptor family (Science 240, 324–326, 327–330, 1988). Androgens with high liposolubility penetrate the target cell membrane by passive diffusion, and bind to the hormone-binding region of AR specifically and with high affinity to form dimers, which bind to an androgen responsive DNA region (androgen response element: ARE) localized upstream from a particular gene. As a result, transcription of the target gene is initiated to induce the expression of mRNA, thereby producing a functional protein responsible for an androgenic action, thus exhibiting this action (Trend in Endocrinology and Metabolism 9, 317–324, 1998). In connection with this mechanism, compounds which bind to AR and show the same actions as natural ligands such as testosterone are defined as agonists, while compounds which inhibit their action are named antagonists.

As the AR agonists, androgen steroid preparations, such as testosterone esters and their derivatives, are currently used in the treatment of male hypogonadism, wasting diseases (malignant tumor, trauma, chronic renal disease, burns), and osteoporosis.

However, these androgen steroid preparations can cause side effects inherent in steroid preparations, such as hepatic dysfunction and gastrointestinal disorder, and may develop androgen-dependent tumor (e.g. prostatic cancer) or prostatic hypertrophy, or aggravate symptoms of these diseases, because they act excessively on the prostate if used in male patients, especially in elderly patients. If these preparations are administered to female patients, they pose major problems of virilizing actions, such as changes in the vocal cord (male-like hoarseness), hypertrichosis of the body trunk, alopecia and acne.

Hence, nonsteroidal AR agonists, which do not show excessive action on the prostate and are minimal in side effects, are desired for the treatment of hypogonadism, and have been under research and development. However, no compounds recognized throughout the world have been created.

For the treatment of wasting disease and osteoporosis, the desired AR agonists are those which do not show excessive action on the prostate, but exhibit potent AR agonism toward skeletal muscle tissue and bone tissue. However, such compounds have not been created.

As AR antagonists, steroidal anti androgen preparations, such as chlormadinone acetate and cyproterone acetate, which are gestagen derivatives, have been used as therapeutic agents. It has been pointed out, however, that these steroid preparations accelerate the negative feedback mechanism of the hypothalamic-pituitary axis by their progesterone action, thereby lowering the blood testosterone level and decreasing sexual function and libido (Drugs Aging 5, 59–80, 1994).

Thus, AR antagonists, as nonsteroidal synthetic compounds diminished in the side effects of the steroids, are desired.

The present invention has been accomplished in view of the therapies of and therapeutic researches on the diseases mediated through AR. The objects of the present invention are to provide novel nonsteroidal compounds and pharmacologically acceptable salts thereof, which are free from the side effects observed with androgen steroid preparations, have a specific and strong binding affinity for AR and exhibit AR agonism or antagonism; and to provide pharmaceutical compositions comprising these compounds or salts as active ingredients.

DISCLOSURE OF THE INVENTION

The inventors of the present invention conducted in-depth studies in an attempt to attain the above objects. As a result, they have found that tetrahydroquinoline compounds of the following formula (I) (hereinafter referred to as "compounds of the present invention") have AR agonism or antagonism, have excellent therapeutic effects on AR-mediated diseases, particularly by not acting excessively on the prostate as AR agonists but by showing potent action on skeletal muscle tissue and bone tissue. Based on these findings, they have accomplished this invention.

That is, the present invention relates to a tetrahydroquinoline compound represented by the following formula (I) or pharmacologically acceptable salts thereof:

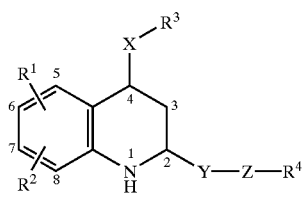

wherein R¹ and R² each independently represent a hydrogen atom, an alkyl group having 1–9 carbon atoms, an alkoxy group having 1–9 carbon atoms, a halogen atom, a nitro group, —NR⁵R⁶ (wherein R⁵ and R⁶ each independently represent a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom and a nitro group, an aryl or heteroaryl group which may optionally be substituted by one or more members selected from the group consisting of an alkyl group having 1–9 carbon atoms, an alkoxy group having 1–9 carbon atoms, a halogen atom and a nitro group, a formyl group, an aliphatic acyl group having 2–5 carbon atoms, an aliphatic acyloxy group having 2–5 carbon atoms, an aromatic acyl group, an alkylsulfonyl group having 1–4 carbon atoms, an arylsulfonyl group, an alkoxycarbonyl group having 2–5 carbon atoms, a hydroxyoxalyl group, or an alkoxyoxalyl group having 3–7 carbon atoms), a carboxyl group, an alkoxycarbonyl group having 2–5 carbon atoms, an amido group, an alkylamido group having 2–5 carbon atoms, an alkylthio group having 1–4 carbon atoms, an alkylsulfinyl group having 1–4 carbon atoms, an alkylsulfonyl group having 1–4 carbon atoms, a cyano group, a sulfamoyl group, an alkylsulfamoyl group having 1–4 carbon atoms, an amidino group, or an alkyl or alkoxy group having 1–5 carbon atoms which has been substituted by fluorine atom(s);

X represents —O—, —OCO—, —OSO₂—, —S—, —SCO—, —SO—, —SO₂—, —NR⁷—, —NR⁷CO—, —NR⁷SO₂—, —NR⁷CONH—, —NR⁷CSNH—, —NR⁷COO— or —NR⁷COCO— (wherein R⁷ represents a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxyalkyl group having 2–5 carbon atoms, or an aryl or heteroaryl group which may optionally be substituted by one or more members selected from the group consisting of an alkyl group having 1–9 carbon atoms, an alkoxy group having 1–9 carbon atoms, a halogen atom, and a nitro group);

R³ represents a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxyalkyl group having 2–5 carbon atoms, or an aryl or heteroaryl group which may optionally be substituted by R⁸ (wherein R⁸ represents an alkyl group having 1–9 carbon atoms, an alkoxy group having 1–9 carbon atoms, a halogen atom or a nitro group), provided that when X is NR⁷, R³ and R⁷ may, together with the nitrogen atom to which they are bonded, form a 3- to 6-membered cyclic amino group or a 4- to 10-membered cyclic imido group;

Y represents an alkylene group having 1–9 carbon atoms which may optionally be substituted by alkyl group(s) having 1–9 carbon atoms, cycloalkyl group(s) having 3–7 carbon atoms, hydroxyl group(s), alkoxy group(s) having 1–9 carbon atoms or —NR⁹R¹⁰ (wherein R⁹ and R10 each independently have the same meaning as R⁵);

Z represents a single bond, —O—, —OCO—, —OSO₂—, —S—, —SCO—, —SO—, —SO₂—, —NR¹¹—, —NR¹¹CO—, —NR¹¹SO₂—, —NR¹¹CONH—, —NR¹¹CSNH—, —NR¹¹COO— or —NR¹¹COCO— (wherein R¹¹ represents a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxyalkyl group having 2–5 carbon atoms, or an aryl or heteroaryl group which may optionally be substituted by R¹² (wherein R¹² is an alkyl group having 1–9 carbon atoms, an alkoxy group having 1–9 carbon atoms, a halogen atom, a nitro group, an aryl or heteroaryl group which may optionally be substituted by one or more members selected from the group consisting of an alkyl group having 1–9 carbon atoms, an alkoxy group having 1–9 carbon atoms, a halogen atom, and a nitro group, —NR¹³R¹⁴ (wherein R¹³ and R¹⁴ each independently have the same meaning as R⁵), a carboxyl group, an alkoxycarbonyl group having 2–5 carbon atoms, an amido group, an alkylamido group having 2 -5 carbon atoms, an alkylthio group having 1–4 carbon atoms, an alkylsulfinyl group having 1–4 carbon atoms, an alkylsulfonyl group having 1–4 carbon atoms, a cyano group, a sulfamoyl group, an alkylsulfamoyl group having 1–4 carbon atoms, or an alkyl or alkoxy group having 1–5 carbon atoms which has been substituted by fluorine atom(s))); and R⁴ represents a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxy group having 1–9 carbon atoms, an alkoxyalkyl group having 2–5 carbon atoms, a halogen atom, a silyl group substituted by hydrocarbon group(s), or an aryl or heteroaryl group which may optionally be substituted by R¹⁵ (wherein R¹⁵ independently has the same meaning as R¹²), provided that when Z is other than a single bond, R⁴ is not a halogen atom. The present invention also relates to a pharmaceutical composition, and an androgen receptor modulator, each comprising the tetrahydroquinoline compound of the formula (I) or pharmacologically acceptable salts thereof as the active ingredient.

BEST MODE FOR CARRYING OUT THE INVENTION

The substituents in the formula (I) will be described.

Examples of the "alkyl group having 1–9 carbon atoms" are straight chain or branched chain alkyl groups, such as a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, an n-hexyl group, a 3,3-dimethylbutyl group, a 2-ethylbutyl group, an n-heptyl group, a 2-methylhexyl group, an n-octyl group, a 2-propylpentyl group, and an n-nonyl group.

Examples of the "alkoxy group having 1–9 carbon atoms" are straight chain or branched chain alkoxy groups, such as a methoxy group, an ethoxy group, an n-propoxy group, an isopropoxy group, an n-butoxy group, an isobutoxy group, a tert-butoxy group, a sec-butoxy group, an n-pentyloxy group, a tert-amyloxy group, a 3-methylbutoxy group, a neopentyloxy group, an n-hexyloxy group, a 3,3-dimethylbutoxy group, a 2-ethylbutoxy group, an n-heptyloxy group, a 2-methylhexyloxy group, an n-octyloxy group, a 2-propylpentyloxy group, and an n-nonyloxy group.

Examples of the "halogen atom" are a fluorine atom, a chlorine atom, a bromine atom, and an iodine atom.

Examples of the "cycloalkyl group having 3–7 carbon atoms" are a cyclopropyl group, a cyclobutyl group, a cyclopentyl group, a cyclohexyl group, and a cycloheptyl group.

Examples of the "aralkyl group having 7–9 carbon atoms" are a benzyl group, a phenethyl group, and a phenylpropyl group.

Examples of the substituted aralkyl group having 7–9 carbon atoms in the "aralkyl group having 7–9 carbon atoms which may optionally be substituted" include a 4-fluorobenzyl group.

Examples of the "aryl group" are a phenyl group, a 1-naphthyl group, and a 2-naphthyl group.

Examples of the substituted aryl group in the "aryl group which may optionally be substituted" include a 4-nitrophenyl group, a 4-fluorophenyl group, and a 2,5-difluorophenyl group.

Examples of the "heteroaryl group" are a furyl group, and a pyridyl group.

Examples of the "aliphatic acyl group having 2–5 carbon atoms" are straight chain or branched chain aliphatic acyl groups, such as an acetyl group, a propionyl group, a butyryl group, an isobutyryl group, a valeryl group, an isovaleryl group, and a pivaloyl group.

Examples of the "aliphatic acyloxy group having 2–5 carbon atoms" are straight chain or branched chain aliphatic acyloxy groups, such as an acetoxy group, a propionyloxy group, a butyryloxy group, an isobutyryloxy group, a valeryloxy group, an isovaleryloxy group, and a pivaloyloxy group.

Examples of the "aromatic acyl group" are a benzoyl group and a toluoyl group.

Examples of the "alkylsulfonyl group having 1–4 carbon atoms" are straight chain or branched chain alkylsulfonyl groups, such as a methanesulfonyl group, an ethanesulfonyl group, an n-propylsulfonyl group, an isopropylsulfonyl group, an n-butylsulfonyl group, an isobutylsulfonyl group, a tert-butylsulfonyl group, and a sec-butylsulfonyl group.

Examples of the "arylsulfonyl group" are a benzenesulfonyl group and a toluenesulfonyl group.

Examples of the "alkoxycarbonyl group having 2–5 carbon atoms" are straight chain or branched chain alkoxycarbonyl groups, such as a methoxycarbonyl group, an ethoxycarbonyl group, an n-propoxycarbonyl group, an isopropoxycarbonyl group, an n-butoxycarbonyl group, an isobutoxycarbonyl group, a tert-butoxycarbonyl group, and a sec-butoxycarbonyl group.

Examples of the "alkoxyoxalyl group having 3–7 carbon atoms" are straight chain or branched chain alkoxyoxalyl groups, such as a methoxyoxalyl group, an ethoxyoxalyl group, an n-propoxyoxalyl group, an isopropoxyoxalyl group, an n-butoxyoxalyl group, an isobutoxyoxalyl group, a tert-butoxyoxalyl group, a sec-butoxyoxalyl group, an n-pentyloxyoxalyl group, a 3-methylbutoxyoxalyl group, and a neopentyloxyoxalyl group.

Examples of the "alkylamido group having 2–5 carbon atoms" are straight chain or branched chain alkylamido groups, such as a methylamido group, an ethylamido group, an n-propylamido group, an isopropylamido group, an n-butylamido group, an isobutylamido group, a tert-butylamido group, a sec-butylamido group, an n-pentylamido group, and a tert-amylamido group.

Examples of the "alkylthio group having 1–4 carbon atoms" are straight chain or branched chain alkylthio groups, such as a methylthio group, an ethylthio group, an n-propylthio group, an isopropylthio group, an n-butylthio group, an isobutylthio group, a tert-butylthio group, and a sec-butylthio group.

Examples of the "alkylsulfinyl group having 1–4 carbon atoms" are straight chain or branched chain alkylsulfinyl groups, such as a methanesulfinyl group, an ethanesulfinyl group, an n-propylsulfinyl group, an isopropylsulfinyl group, an n-butylsulfinyl group, an isobutylsulfinyl group, a tert-butylsulfinyl group, and a sec-butylsulfinyl group.

Examples of the "alkylsulfamoyl group having 1–4 carbon atoms" are straight chain or branched chain alkylsulfamoyl groups, such as a methanesulfamoyl group, an ethanesulfamoyl group, an n-propylsulfamoyl group, an isopropylsulfamoyl group, an n-butylsulfamoyl group, an isobutylsulfamoyl group, a tert-butylsulfamoyl group, and a sec-butylsulfamoyl group.

Examples of the "alkyl or alkoxy group having 1–5 carbon atoms which has been substituted by fluorine atom(s)" are a trifluoromethyl group, a trifluoromethoxy group, and a tetrafluoroethoxy group.

Examples of the "alkylene group having 1–9 carbon atoms" are a methylene group, an ethylene group, a tetramethylene group, a pentamethylene group, and a hexamethylene group.

Examples of the substituted alkylene group having 1–9 carbon atoms in the "alkylene group having 1–9 carbon atoms which may optionally be substituted" are a dimethylethylene group, and a monomethylethylene group.

Examples of the "alkoxyalkyl group having 2–5 carbon atoms" are straight chain or branched chain alkoxyalkyl groups, such as a methoxymethyl group, an ethoxymethyl group, an n-propoxymethyl group, an isopropoxymethyl group, an n-butoxymethyl group, an isobutoxymethyl group, a tert-butoxymethyl group, a sec-butoxymethyl group, a methoxyethyl group, an ethoxyethyl group, an n-propoxyethyl group, an isopropoxyethyl group, a methoxypropyl group, an ethoxypropyl group, and a methoxybutyl group.

The "silyl group substituted by hydrocarbon group(s)" refers to a silyl group substituted, for example, by alkyl group(s) having 1–6 carbon atoms and/or aryl group(s). Examples of such a substituted silyl group are a trimethylsilyl group, a triethylsilyl group, a triisopropylsilyl group, a dimethylisopropylsilyl group, a tert-butyldimethylsilyl group, a tert-butyldiphenylsilyl group, and a triphenylsilyl group.

Examples of a case in which "$R^3$ and $R^7$, together with the nitrogen atom to which they are bonded, form a 3- to 6-membered cyclic amino group" are pyrrolidine and piperidine.

Examples of a case in which "$R^3$ and $R^7$, together with the nitrogen atom to which they are bonded, form a 4- to 10-membered cyclic imido group" are succinimide, phthalimide, and 1,2-cyclohexanedicarboxyimide.

Preferred modes for the compounds of the formula (I) include, for example, the following:

The preferred substitution position of $R^1$ and $R^2$ is the 6-position of the tetrahydroquinoline ring, and $R^1$ and $R^2$ are preferably such that one of them is a hydrogen atom, while the other is a nitro group or a cyano group.

X is preferably —O—, —S—, —SO—, —SO$_2$—, —NR$^7$—, —NR$^7$CO—, —NR$^7$SO$_2$—, —NR$^7$CONH—, or —NR$^7$CSNH— (wherein $R^7$ is as defined earlier), more preferably —O—, —S—, —SO—, —SO$_2$—, or —NR$^7$—, and even more preferably —O—, —S—, or —NR$^7$—.

$R^7$ is preferably a hydrogen atom, an alkyl group having 1–9 carbon atoms, an aralkyl group having 7–9 carbon atoms, an aryl group, or a heteroaryl group, more preferably a hydrogen atom, or an alkyl group having 1–3 carbon atoms, and even more preferably a hydrogen atom, a methyl group or an ethyl group.

$R^3$ is preferably a hydrogen atom, an alkyl group having 1–9 carbon atoms, an aralkyl group having 7–9 carbon atoms, or an aryl or heteroaryl group which may optionally be substituted by $R^8$ (wherein $R^8$ represents an alkyl group having 1–9 carbon atoms, an alkoxy group having 1–9 carbon atoms, a halogen atom or a nitro group), provided that when X is NR$^7$, $R^3$ and $R^7$ may, together with the nitrogen atom to which they are bonded, form a 3- to 6-membered cyclic amino group or a 4- to 10-membered cyclic imido group. More preferably, $R^3$ is an alkyl group having 1–3 carbon atoms, an aralkyl group having 7–9 carbon atoms, or an aryl group, and even more preferably, $R^3$ is a methyl group or an ethyl group.

In the definition of Y, the number of the substituents which may optionally take part in substitution is preferably 1 to 3, and preferred examples of the substituent are a methyl group and an ethyl group.

Y is preferably an alkylene group having 1–9 carbon atoms that may optionally be substituted by alkyl group(s) having 1–9 carbon atoms, more preferably an alkylene group having 1–4 carbon atoms that may optionally be substituted by alkyl group(s) having 1–2 carbon atoms, further preferably a dimethylethylene or monomethylethylene group, and still further preferably —C(CH$_3$)$_2$—CH$_2$—.

ZR$^4$ is preferably such that when Z is —O—, —OCO—, —OSO$_2$—, —NH—, —NHCO—, —NHSO$_2$—, —NHCONH—, —NHCSNH—, or —NHCOO—, $R^4$ is a hydrogen atom, an alkyl group having 1–9 carbon atoms, an aralkyl group having 7–9 carbon atoms, an alkoxyalkyl group having 2–5 carbon atoms, a silyl group substituted by hydrocarbon group(s), or an aryl or heteroaryl group which may optionally be substituted by $R^{15}$ (wherein $R^{15}$ is as defined previously). More preferably, ZR$^4$ is such that when Z is —O— or —OCO—, $R^4$ is a hydrogen atom, an alkyl group having 1–4 carbon atoms, or an aryl group which may optionally be substituted by $R^{15}$. Even more preferably, ZR$^4$ is a hydroxyl group.

In this case, $R^{15}$ is preferably an alkyl group having 1–9 carbon atoms, an alkoxy group having 1–9 carbon atoms, a halogen atom, or an acetamido group, and more preferably a halogen atom or an acetamido group.

Preferred combinations of the substituents in the formula (I) are such that $R^1$ is a nitro group or a cyano group; $R^2$ is a hydrogen atom; X is —O—, —S—, —SO—, —SO$_2$—, —NR$^7$—, —NR$^7$CO—, —NR$^7$SO$_2$—, —NR$^7$CONH—, or —NR$^7$CSNH— (wherein $R^7$ is preferably a hydrogen atom, an alkyl group having 1–9 carbon atoms, an aralkyl group having 7–9 carbon atoms, an aryl group, or a heteroaryl group); $R^3$ is a hydrogen atom, an alkyl group having 1–9 carbon atoms, an aralkyl group having 7–9 carbon atoms, or an aryl or heteroaryl group which may optionally be substituted by $R^8$ (wherein $R^8$ is an alkyl group having 1–9 carbon atoms, an alkoxy group having 1–9 carbon atoms, a halogen atom or a nitro group), provided that when X is NR$^7$, $R^3$ and $R^7$ may, together with the nitrogen atom to which they are bonded, form a 3- to 6-membered cyclic amino group or a 4- to 10-membered cyclic imido group; Y is an alkylene group having 1–9 carbon atoms that may optionally be substituted by alkyl group(s) having 1–9 carbon atoms; Z is —O—, —OCO—, —OSO$_2$, —NH—, —NHCO—, —NHSO$_2$—, —NHCONH—, —NHCSNH—, or —NHCOO—; $R^4$ is a hydrogen atom, an alkyl group having 1–9 carbon atoms, an aralkyl group having 7–9 carbon atoms, an alkoxyalkyl group having 2–5 carbon atoms, a silyl group substituted by hydrocarbon group(s), or an aryl or heteroaryl group that may optionally be substituted by $R^{15}$ (wherein $R^{15}$ is an alkyl group having 1–9 carbon atoms, an alkoxy group having 1–9 carbon atoms, a halogen atom, or an acetamido group).

More preferred combinations are such that $R^1$ is a nitro group or a cyano group; $R^2$ is a hydrogen atom; X is —O—, —S—, —SO—, —SO$_2$—, or —NR$^7$— (wherein $R^7$ is preferably a hydrogen atom, or an alkyl group having 1–3 carbon atoms); $R^3$ is an alkyl group having 1–3 carbon atoms, an aralkyl group having 7–9 carbon atoms, or an aryl group; Y is an alkylene group having 1–4 carbon atoms that may optionally be substituted by alkyl group(s) having 1–2 carbon atoms; Z is —O— or —OCO—; $R^4$ is a hydrogen atom, an alkyl group having 1–4 carbon atoms, or an aryl group that may optionally be substituted by $R^{15}$ (wherein $R^{15}$ is preferably a halogen atom or an acetamido group).

The most preferred combinations are such that $R^1$ is a nitro group or a cyano group; $R^2$ is a hydrogen atom; X is —O—, —S—, or —NR$^7$— (wherein $R^7$ is preferably a hydrogen atom, a methyl group or an ethyl group); $R^3$ is a methyl group or an ethyl group; Y is a dimethylethylene group or a monomethylethylene group; and ZR$^4$ is a hydroxyl group.

Particularly preferred compounds of the present invention are as follows:

2-(4-Ethoxy-6-nitro-1,2,3,4-tetrahydroquinolin-2-yl)-2-methylpropan-1-ol (Example 3)

2-(4-Ethylsulfanyl-6-nitro-1,2,3,4-tetrahydroquinolin-2-yl)-2-methylpropan-1-ol (Example 4)

2-Methyl-2-(6-nitro-4-phenylsulfanyl-1,2,3,4-tetrahydroquinolin-2-yl)propan-1-ol (Example 5)

Acetic acid 2-(4-dimethylamino-6-nitro-1,2,3,4-tetrahydroquinolin-2-yl)-2-methyl-propyl ester (Example 9)

4-Fluorobenzoic acid 2-(4-dimethylamino-6-nitro-1,2,3,4-tetrahydroquinolin-2-yl)-2-methyl-propyl ester (Example 11)

2-(4-Dimethylamino-6-nitro-1,2,3,4-tetrahydroquinolin-2-yl)-2-methylpropan-1-ol (Example 23)

2-(4-Benzylamino-6-nitro-1,2,3,4-tetrahydroquinolin-2-yl)-2-methylpropan-1-ol (Example 30)

2-(4-Di-n-propylamino-6-nitro-1,2,3,4-tetrahydroquinolin-2-yl)-2-methylpropan-1-ol (Example 33)

If asymmetric carbon is present in the compound of the present invention represented by the formula (I), its racemic compounds, diastereomers, and individual optical isomers are all included in the present invention. If its geometrical isomers are present, (E) compounds, (Z) compounds, and mixtures of them are all included in the present invention.

The salts of the compounds of the present invention represented by the formula (I) are not limited, as long as they are those which are pharmacologically acceptable. Their examples include hydrohalogenic acid salts, such as hydrofluorides, hydrochlorides, hydrobromides, and hydroiodides, inorganic acid salts, such as nitrates, perchlorates, sulfates, phosphates, and carbonates, lower alkylsulfonic acid salts, such as methanesulfonates, trifluoromethanesulfonates, and ethanesulfonates, arylsulfonic acid salts, such as benzenesulfonates and p-toluenesulfonates, carboxylic acid salts, such as acetates, fumarates, succinates, citrates, tartrates, oxalates, and maleates, amino acid salts, such as glycine salts, alanine salts, glutamates, and aspartates, and alkali metal salts, such as sodium salts and potassium salts.

Solvates of the compounds of the present invention are also included in the present invention. Examples of the solvates are solvates with solvents, such as acetone, 2-butanol, 2-propanol, ethanol, ethyl acetate, tetrahydrofuran, and diethyl ether.

The tetrahydroquinoline compounds of the present invention can be produced by the following methods:

[Production Method 1]

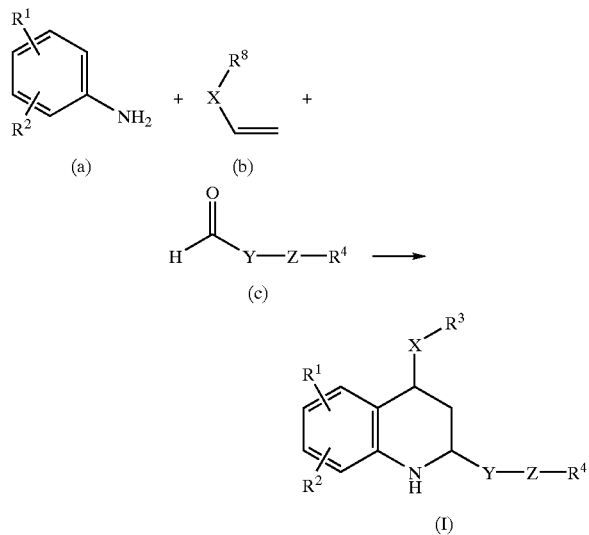

where all the symbols are as defined above, except for a case where —X—$R^3$ represents $NH_2$, and cases where -Z-$R^4$ represents SH, $SOR^4$, $SO_2R^4$ or $NH_2$.

The compound of the present invention, expressed by the formula (I), can be produced by reacting the compounds represented by the formulas (a), (b) and (c) in an inert solvent in the presence or absence of an acid.

The compounds represented by the formulas (a), (b) and (c) can be obtained as commercially available reagents, or by easy derivation therefrom by routine chemical reactions.

The present reaction will be described concretely. Any type of acids, organic or inorganic, are preferred. For example, acetic acid, trifluoroacetic acid, p-toluenesulfonic acid, hydrochloric acid, sulfuric acid, tin tetrachloride, titanium tetrachloride, boron trifluoride diethyl etherate, diethylaluminum chloride, or ethylaluminum dichloride is used. The acid is preferably used in an amount of a catalytic amount to 10 equivalents with respect to the compound represented by the formula (a). The reaction solvent is not limited, as long as it is a solvent which does not markedly impede the present reaction. The preferred reaction solvent is dichloromethane, chloroform, 1,2-dichloroethane, hexane, benzene, toluene, dioxane, tetrahydrofuran, acetonitrile, methanol, ethanol, water or a mixture of these solvents. The reaction temperature is preferably −20 to 100° C., and the reaction time is preferably 5 minutes to 48 hours.

[Production Method 2]

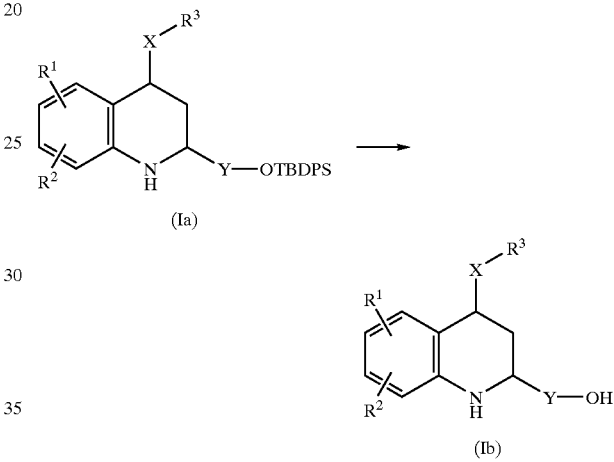

where TBDPS signifies a tert-butyldiphenylsilyl group, and the other symbols are as defined earlier.

Of the compounds of the present invention, the compound represented by the formula (Ib) can be produced by deprotection of the compound represented by the formula (Ia) by means of hydrolysis in the presence of an acid or a base or treatment with a fluoride, in addition to the method shown in Production Method 1.

The present reaction will be described concretely. Any type of acids, organic or inorganic, are preferred. For example, acetic acid, trifluoroacetic acid, hydrochloric acid, or sulfuric acid is used. Either type of bases, metal hydroxides or metal carbonates, are preferred. For example, sodium hydroxide, potassium hydroxide, barium hydroxide, sodium carbonate, or potassium carbonate is used. As the fluoride, an aqueous hydrogen fluoride solution, or tetrabutylammonium fluoride, for example, is used. The acid, base or fluoride is preferably used in an amount of 1 to 50 equivalents with respect to the compound represented by the formula (Ia). The reaction solvent is not limited, as long as it is a solvent which does not markedly impede the present reaction. The preferred reaction solvent is dichloromethane, chloroform, 1,2-dichloroethane, hexane, benzene, toluene, dioxane, tetrahydrofuran, acetonitrile, methanol, ethanol, water or a mixture of these solvents. The reaction temperature is preferably −40 to 100° C., and the reaction time is preferably 30 minutes to 24 hours.

[Production Method 3]

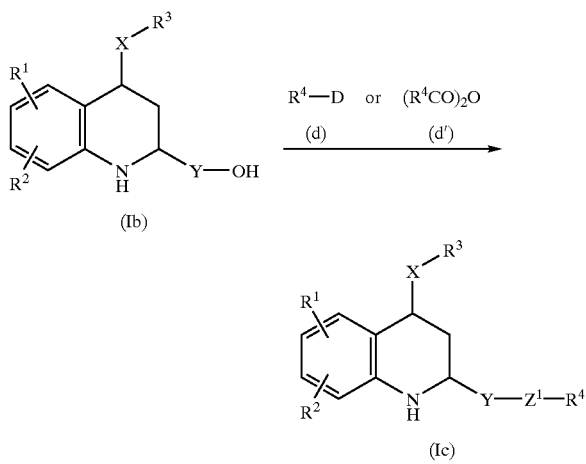

where D represents a halogen atom, a chlorosulfonyl group or a halogenated carbonyl group, $Z^1$ represents —O—, —OCO— or —OSO$_2$—, and the other symbols are as defined earlier, except for a case where —X—R$^3$ is NH$_2$.

Of the compounds of the present invention, the compound represented by the formula (Ic) can be produced by reacting the compound represented by the formula (Ib) with the compound represented by the formula (d) or (d') without a solvent or in an inert solvent in the presence or absence of a base.

The compounds represented by the formulas (d) and (d') can be obtained as commercially available reagents, or by easy derivation therefrom by routine chemical reactions.

Examples of the "halogenated carbonyl group" are a chlorocarbonyl group and a bromocarbonyl group.

The present reaction will be described concretely. The base is preferably a tertiary amine, and its examples are triethylamine and pyridine. The compound represented by the formula (d) or (d') is preferably used in an amount of 1 to 10 equivalents with respect to the compound represented by the formula (Ib). The base is preferably used in an amount of 1 equivalent to a large excess with respect to the compound represented by the formula (d) or (d'). The reaction solvent is not limited, as long as it is a solvent which does not markedly impede the present reaction. The preferred reaction solvent is dichloromethane, chloroform, 1,2-dichloroethane, 1,1,2,2-tetrachloroethane, toluene, dimethylformamide, or tetrahydrofuran. The reaction temperature is preferably 0 to 80° C., and the reaction time is preferably 30 minutes to 12 hours.

[Production Method 4]

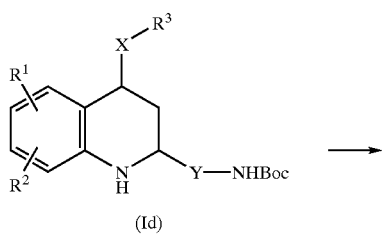

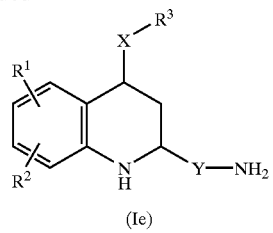

where Boc represents a tert-butoxycarbonyl group, and the other symbols are as defined earlier.

Of the compounds of the present invention, the compound represented by the formula (Ie) can be produced by deprotection of the compound represented by the formula (Id) by means of treatment with an acid.

The present reaction will be described concretely. Any type of acids, organic or inorganic, are preferred. For example, acetic acid, trifluoroacetic acid, p-toluenesulfonic acid, hydrochloric acid, or sulfuric acid is used. The acid is preferably used in an amount of 1 to 50 equivalents with respect to the compound represented by the formula (Id). The reaction solvent is not limited, as long as it is a solvent which does not markedly impede the present reaction. The preferred reaction solvent is dichloromethane, chloroform, 1,2-dichloroethane, hexane, benzene, toluene, dioxane, tetrahydrofuran, acetonitrile, methanol, ethanol, water, or a mixture of these solvents. The reaction temperature is preferably 0 to 100° C., and the reaction time is preferably 30 minutes to 24 hours.

[Production Method 5]

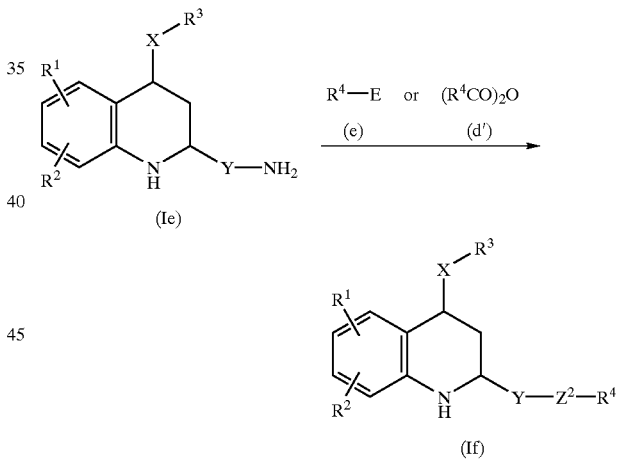

where E represents a chlorosulfonyl group, a halogenated carbonyl group, an isocyanato group, or a thioisocyanato group, $Z^2$ represents —NHCO—, —NHSO$_2$—, —NHCONH—, or —NHCSNH—, and the other symbols are as defined earlier, except for a case where —X—R$^3$ is NH$_2$.

Of the compounds of the present invention, the compound represented by the formula (If) can be produced by reacting the compound represented by the formula (Ie) with the compound represented by the formula (e) or (d') without a solvent or in an inert solvent in the presence or absence of a base.

The compound represented by the formula (e) can be obtained as a commercially available reagent, or by easy derivation therefrom by routine chemical reactions.

Examples of the "halogenated carbonyl group" are a chlorocarbonyl group and a bromocarbonyl group.

The present reaction will be described concretely. The base is preferably a tertiary amine, and its examples are triethylamine and pyridine. The compound represented by the formula (e) or (d') is preferably used in an amount of 1 to 10 equivalents with respect to the compound represented by the formula (Ie). The base is preferably used in an amount of 1 equivalent to a large excess with respect to the compound represented by the formula (e) or (d'). The reaction solvent is not limited, as long as it is a solvent which does not markedly impede the present reaction. The preferred reaction solvent is dichloromethane, chloroform, 1,2-dichloroethane, 1,1,2,2-tetrachloroethane, toluene, dimethylformamide, or tetrahydrofuran. The reaction temperature is preferably 0 to 80° C., and the reaction time is preferably 30 minutes to 24 hours.

[Production Method 6]

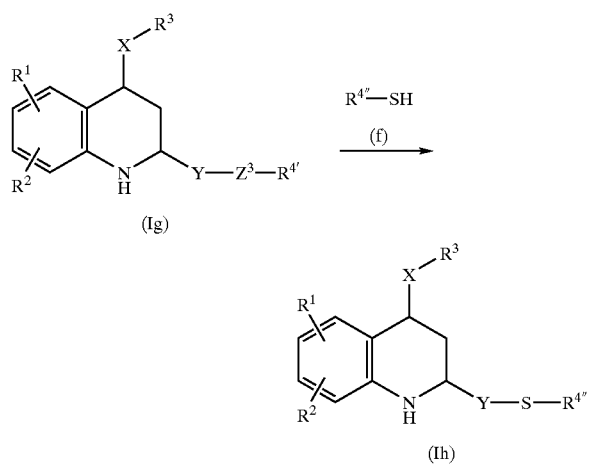

where $Z^3$ represents a single bond, $R^{4'}$ represents a halogen atom, $R^{4''}$ represents $R^4$ other than a halogen atom, and the other symbols are as defined earlier.

Of the compounds of the present invention, the compound represented by the formula (Ih) can be produced by reacting the compound represented by the formula (Ig) with the compound represented by the formula (f) without a solvent or in an inert solvent in the presence or absence of a base.

The compound represented by the formula (f) can be obtained as a commercially available reagent, or by easy derivation therefrom by routine chemical reactions.

The present reaction will be described concretely. The base is, for example, triethylamine, pyridine, sodium hydride, or potassium tert-butoxide. The compound represented by the formula (f) is preferably used in an amount of 1 to 10 equivalents with respect to the compound represented by the formula (Ig). The base is preferably used in an amount of 1 equivalent to a large excess with respect to the compound represented by the formula (f). The reaction solvent is not limited, as long as it is a solvent which does not markedly impede the present reaction. The preferred reaction solvent is dichloromethane, chloroform, 1,2-dichloroethane, 1,1,2,2-tetrachloroethane, toluene, dimethylformamide, or tetrahydrofuran. The reaction temperature is preferably 0 to 100° C., and the reaction time is preferably 5 minutes to 24 hours.

[Production Method 7]

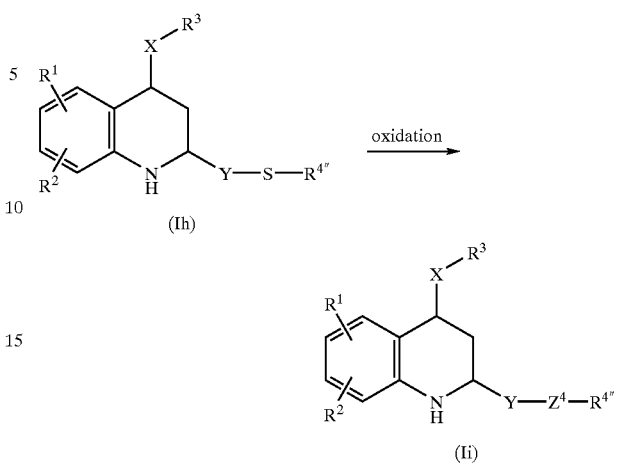

where $Z^4$ represents —SO— or —SO$_2$—, and the other symbols are as defined earlier, except for a case where X is —S— or —SO—.

Of the compounds of the present invention, the compound represented by the formula (Ii) can be produced by oxidizing the compound represented by the formula (Ih) in an inert solvent in the presence of an oxidizing agent.

The present reaction will be described concretely. As the oxidizing agent, peracetic acid or m-chloroperbenzoic acid, for example, is named. The oxidizing agent is preferably used in an amount of 1 equivalent to a large excess with respect to the compound represented by the formula (Ih). The reaction solvent is not limited, as long as it is a solvent which does not markedly impede the present reaction. The preferred reaction solvent is dichloromethane, chloroform, 1,2-dichloroethane, 1,1,2,2-tetrachloroethane, toluene, dimethylformamide, or tetrahydrofuran. The reaction temperature is preferably –20 to 100° C., and the reaction time is preferably 5 minutes to 24 hours.

[Production Method 8]

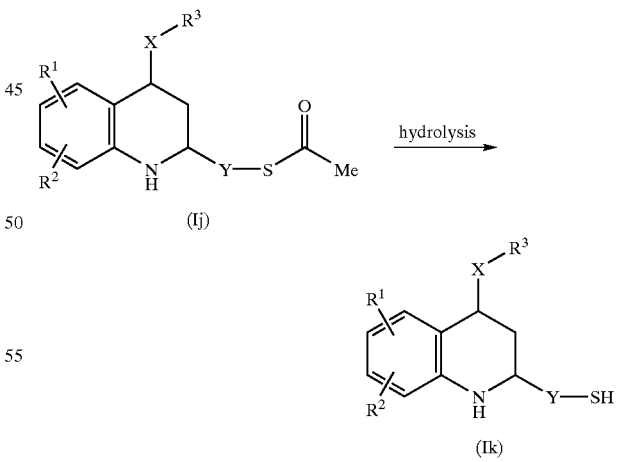

where all the symbols are as defined earlier.

Of the compounds of the present invention, the compound represented by the formula (Ik) can be produced by hydrolyzing the compound represented by the formula (Ij) in the usual manner in the presence of an acid or a base.

The present reaction will be described concretely. Any type of acids, organic or inorganic, are preferred. For example, acetic acid, trifluoroacetic acid, hydrochloric acid, or sulfuric acid is named. Either type of bases, metal hydroxides or metal carbonates, are preferred. For example; sodium hydroxide, potassium hydroxide, barium hydroxide, sodium carbonate, or potassium carbonate is named. The acid or base is preferably used in an amount of 1 to 50 equivalents with respect to the compound represented by the formula (Ij). The reaction solvent is not limited, as long as it is a solvent which does not markedly impede the present reaction. The preferred reaction solvent is water, methanol, ethanol, tetrahydrofuran, dioxane, chloroform, 1,2-dichloroethane, or a mixture of these solvents. The reaction temperature is preferably 0 to 100° C., and the reaction time is preferably 30 minutes to 24 hours.

[Production Method 9]

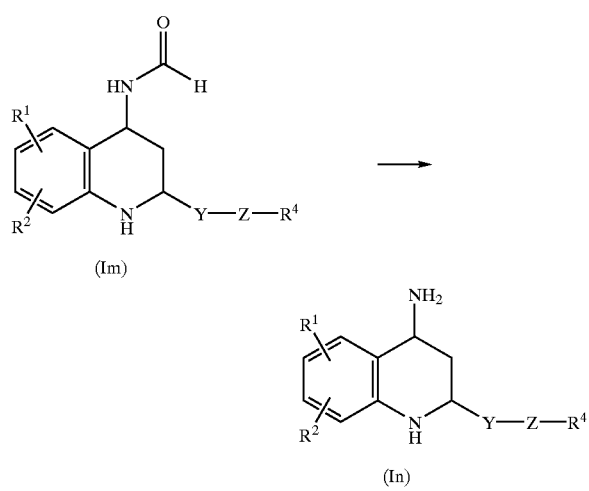

where all the symbols are as defined earlier.

Of the compounds of the present invention, the compound represented by the formula (In) can be produced by deprotection of the compound represented by the formula (Im) by means of hydrolysis in the presence of an acid or a base, or catalytic reduction in the presence of a catalyst.

The present reaction will be described concretely. Any type of acids, organic or inorganic, are preferred. For example, acetic acid, trifluoroacetic acid, p-toluenesulfonic acid, hydrochloric acid, or sulfuric acid is named. Either type of bases, organic bases or inorganic bases, are preferred. For example, methylhydrazine or sodium hydroxide is named. The acid or base is preferably used in an amount of 1 equivalent to a large excess with respect to the compound represented by the formula (Im). The catalyst used in the catalytic reduction reaction is, for example, 5% palladium carbon or 10% palladium carbon. The catalyst is preferably used in an amount of a catalytic amount to 10 equivalents with respect to the compound represented by the formula (Im). The hydrogen pressure is preferably 1 to 5 atmospheres. The reaction solvent is not limited, as long as it is a solvent which does not markedly impede the present reaction. The preferred reaction solvent is dichloromethane, chloroform, 1,2-dichloroethane, hexane, benzene, toluene, dioxane, tetrahydrofuran, acetonitrile, methanol, ethanol, water, or a mixture of these solvents. The reaction temperature is preferably 0 to 100° C., and the reaction time is preferably 30 minutes to 48 hours.

[Production Method 10]

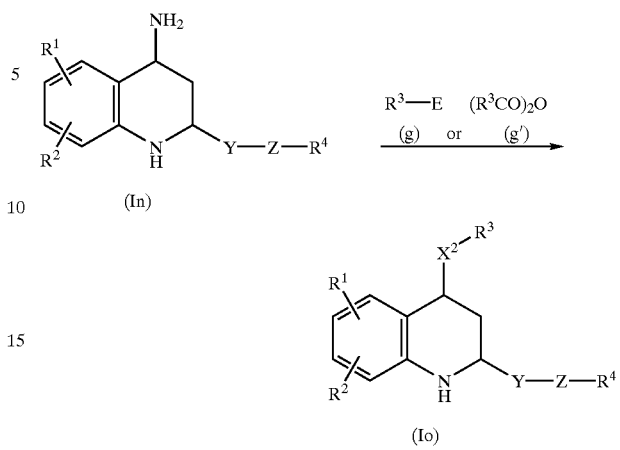

where $X^2$ represents —NHCO—, —NHSO$_2$—, —NHCONH—, or —NHCSNH—, and the other symbols are as defined earlier, except for a case where -Z-R$^4$ is NH$_2$.

Of the compounds of the present invention, the compound represented by the formula (Io) can be produced by reacting the compound represented by the formula (In) with the compound represented by the formula (g) or (g') without a solvent or in an inert solvent in the presence or absence of a base.

The compounds represented by the formulas (g) and (g') can be obtained as commercially available reagents, or by easy derivation therefrom by routine chemical reactions.

The reaction conditions for the present reaction can be set in the same manner as in Production Method 5.

[Production Method 11]

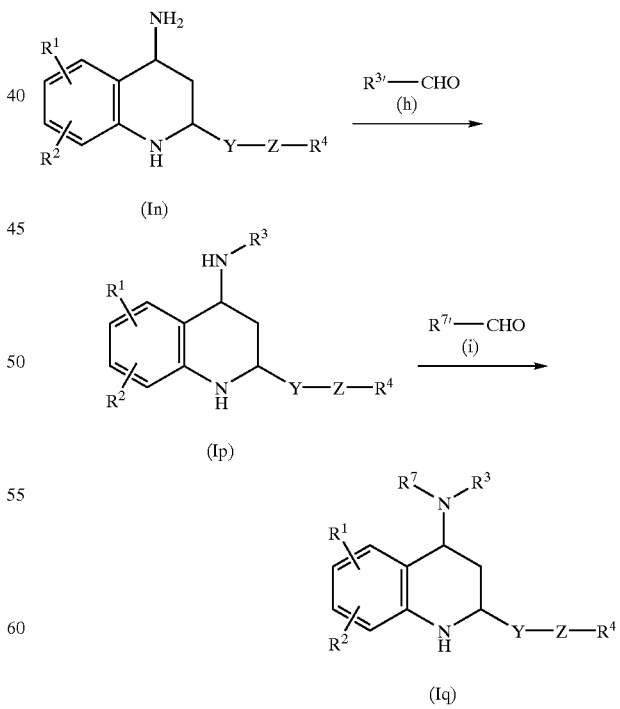

where R$^3$ represents a hydrogen atom, an alkyl group having 1–8 carbon atoms, an aralkyl group having 7–8 carbon atoms, an alkoxyalkyl group having 2–4 carbon atoms, or an aryl group, $R^{7'}$ represents a hydrogen atom, an alkyl group having 1–8 carbon atoms, an aralkyl group having 7–8 carbon atoms, an alkoxyalkyl group having 2–4 carbon atoms, or an aryl group, and the other symbols are as defined earlier, except for a case where $-Z-R^4$ is $NH_2$.

Of the compounds of the present invention, the compounds represented by the formulas (Ip) and (Iq) can be produced by the reductive amination of the compound represented by the formula (In) with the compounds represented by the formulas (h) and (i) in the usual manner without a solvent or in an inert solvent in the presence or absence of an acid.

The compounds represented by the formulas (h) and (i) can be obtained as commercially available reagents, or by easy derivation therefrom by routine chemical reactions.

The present reaction will be described concretely. Any type of acids, organic or inorganic, are preferred. For example, formic acid, acetic acid, trifluoroacetic acid, hydrochloric acid, or sulfuric acid is named. As the reducing agent, inorganic metallic reagents or organic metallic reagents are preferred. Examples include palladium, zinc, sodium cyanoborohydride, sodium triacetoxyborohydride, and aluminum lithium hydride. The compound represented by the formula (h) or (i) is preferably used in an amount of 1 equivalent to an excess with respect to the compound represented by the formula (In) or (Ip), respectively. Particularly, the compound of the formula (Iq), in which $R^3$ and $R^7$ are the same, can be produced in a single step by using an excess of the compound represented by the formula (h). The acid or base is preferably used in an amount of 1 equivalent to a large excess with respect to the compound represented by the formula (In) or (Ip). The reaction solvent is not limited, as long as it is a solvent which does not markedly impede the present reaction. The preferred reaction solvent is methanol, ethanol, tetrahydrofuran, dioxane, chloroform, 1,2-dichloroethane, or a mixture of these solvents. The reaction temperature is preferably –78 to 100° C., and the reaction time is preferably 30 minutes to 24 hours.

[Production Method 12]

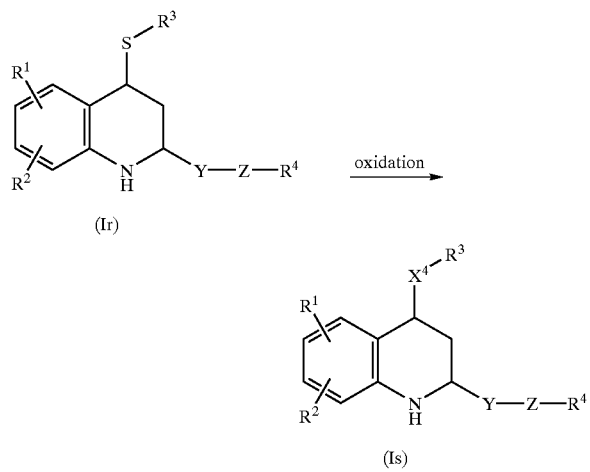

where $X^4$ represents —SO— or —$SO_2$—, and the other symbols are as defined earlier, except for a case where Z is —S— or —SO—.

Of the compounds of the present invention, the compound represented by the formula (Is) can be produced by oxidizing the compound represented by the formula (Ir) in an inert solvent in the presence of an oxidizing agent.

The reaction conditions for the present reaction can be set in the same manner as in Production Method 7.

The compounds of the present invention, which are produced by the above-described methods, are isolated and purified as free compounds, their salts, their hydrates, various solvates thereof, such as ethanolates, or crystalline polymorphic substances. The pharmacologically acceptable salts of the compounds according to the present invention can be produced by the general salt-forming reaction. The isolation and purification are performed by applying chemical operations, such as extractive fractionation, crystallization, and various chromatographic techniques. The stereochemically pure optical isomers can be synthesized by using suitable starting compounds, or by optical resolution of racemic compounds.

The tetrahydroquinoline compounds or pharmacologically acceptable salts thereof according to the present invention have an excellent AR modulating action. These substances can be used as active ingredients to form pharmaceuticals or AR modulators. These pharmaceuticals can be widely used in the prophylaxis or treatment of various AR-related diseases.

As the AR-related diseases, the following categories A and B are named:

A. Diseases which can be expected to be cured by the physiological action of androgen: Examples include male hypogonadism, male sexual dysfunction (impotence, male dysspermatogenic sterility), abnormal sex differentiation (male hermaphroditism), male delayed puberty, male infertility, aplastic anemia, hemolytic anemia, sickle cell anemia, idiopathic thrombocytopenic purpura, myelofibrosis, renal anemia, wasting diseases (after operation, malignant tumor, trauma, chronic renal disease, burns, AIDS infection), osteoporosis, abatement of pain in terminal carcinoma of female genitalia, inoperable breast cancer, mastopathy, endometriosis, and female sexual dysfunction.

The tetrahydroquinoline compounds or pharmacologically acceptable salts thereof according to the present invention show a particularly potent action on bone tissues and skeletal muscles. Thus, they are suggested to have a protein anabolic action, and can be used in the prophylaxis or treatment of the diseases described below.

Diseases for which they may be indicated because of their potent action on bone tissues include, for example, primary osteoporosis (senile, postmenopausal and juvenile osteoporosis) and secondary osteoporosis (osteoporosis ascribed to hyperthyroidism, Cushing syndrome (due to steroid treatment), acromegaly, hypogonadism, dysosteogenesis, hypophosphatasemia, osteoporosis of disuse, or diabetes).

Diseases for which they may be indicated because of their potent action on muscular tissues include, for example, wasting diseases (after operation, malignant tumor, trauma, chronic renal disease, burns, AIDS infection).

B. Diseases for which androgen is a precipitating factor: Examples include prostatic cancer, prostatomegaly, virilization, acne, seborrhea, hypertrichosis, alopecia, male precocious puberty, and polycystic ovary syndrome.

For the category A diseases, the compounds of the present invention with AR agonistic action can be used, their preferred examples being compounds of Examples 3, 4, 5, 23 and 30 to be described later.

For the category B diseases, the compounds of the present invention with AR antagonistic action can be used. For example, a compound of Example 33 to be described later was suggested by a Test Example (to be described later) to be an AR antagonist.

The pharmaceuticals of the present invention can be applied widely to these AR-related diseases, and may be applied to diseases which are not exemplified here, if the modulation of AR function is required for them at present or in the future.

The pharmaceuticals of the present invention can be administered orally or parenterally, and may be of the systemic administration type or local administration type.

Their dosage forms are not limited, and can be selected, as desired, according to the route of administration. Their examples include tablets, capsules, sugar-coated tablets, granules, subtle granules, inhalations, suppositories, liquids and solutions, syrups, dry syrups, suspensions, emulsions, lotions, ointments, patches, sprays, gels, nasal drops, eye drops, and injections.

These preparations can be produced by incorporating pharmacologically acceptable carriers, namely, organic or inorganic, solid or liquid vehicles, adjuvants, stabilizers, wetting agents, emulsifying agents, buffers, and other pharmacologically acceptable various additives, into compositions containing the compounds of the present invention.

The dose of the pharmaceutical of the present invention in humans is determined, as desired, according to various conditions, such as the purpose of treatment or prevention, the patient's sex, body weight, and age, the type and severity of the disease, dosage form, the route of administration, and the duration of treatment. The daily dose of the tetrahydroquinoline compound of the present invention is generally 0.01 to 100 mg/kg.

The pharmaceuticals of the present invention may be used in the treatment of androgen receptor-mediated diseases in warm-blooded animals, such as domestic animals, pets, bred animals, or wild animals. The dosage forms and doses in this case can be determined by reference to the dosage forms and doses in humans.

EXAMPLES

The compounds of the present invention and the methods for their production will be described in further detail by working examples. However, the present invention is not to be interpreted restrictedly because of these descriptions.

$^1$H—NMR spectra were recorded on JNM-EX270 Spectrometer (270 MHz, JEOL Ltd.). Chemical shifts (δ) are expressed in ppm downfield from tetramethylsilane (TMS) as an internal standard.

In the structural formulas and tables offered below, Me represents a methyl group, Et an ethyl group, Pr a propyl group, Bu a butyl group, Ph a phenyl group, Bn a benzyl group, and Ac an acetyl group, the remainder being as defined earlier.

Example 1

Production of 2-[2-(tert-butyldiphenylsilanoxy)-1,1-dimethylethyl]-4-ethoxy-6-nitro-1,2,3,4-tetrahydroquinoline

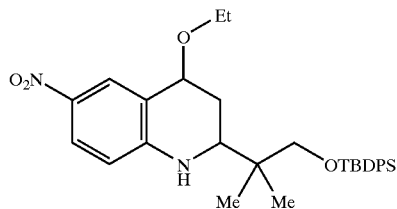

4-Nitroaniline (200 mg), 0.15 ml of ethyl vinyl ether, and 0.1 ml of trifluoroacetic acid were dissolved in 5 ml of acetonitrile, and 500 mg of 3-(tert-butyldiphenylsilanoxy)-2,2-dimethylpropionaldehyde was added at 0° C. After 6 hours of stirring at room temperature, the solvent was distilled off under reduced pressure. The residue was purified by silica gel column chromatography (elution solvent; hexane:ethyl acetate=10:1–8:1) to obtain 34 mg of the title compound. Its physical properties are shown below.

$^1$H—NMR(CDCl$_3$) δ: 0.90(3H, s), 1.02(3H, s), 1.14(9H, s), 1.35 (3H, t, J=7.3 Hz), 1.56(1H, q, J=11.9 Hz), 2.25(1H, br d, J=8.9 Hz), 3.47(1H, d, J=8.9 Hz), 3.56(1H, dd, J=2.9, 11.2 Hz), 3.65(1H, d, J=8.9 Hz), 3.68–3.78(1H, m), 3.80–3.86(1H, m), 4.53(1H, dd, J=4.6, 11.2 Hz), 6.18(1H, d, J=8.9 Hz), 6.22(1H, br s), 7.36–7.51(6H, m), 7.64–7.68(4H, m), 7.88(1H, dd, J=2.6, 8.9 Hz), 8.25(1H, br s).

Example 2

Production of {2-[4-(1,3-dioxo-1,3-dihydroisoindol-2-yl)-6-nitro-1,2,3,4-tetrahydroquinolin-2-yl]-2-methylpropyl}-carbamate tert-butyl Ester

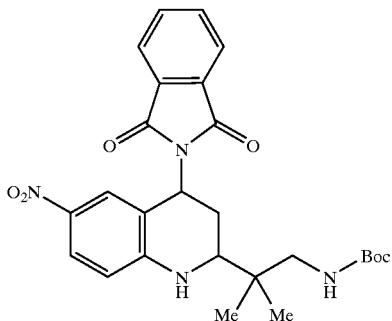

The title compound was obtained in the same manner as in Example 1. Its physical properties are shown below.

$^1$H—NMR(CDCl$_3$) δ: 0.92(3H, s), 0.96(3H, s), 1.41(9H, s), 1.95–2.17(1H, m), 2.62(1H, q, J=12.2 Hz), 2.75–2.85 (1H, m), 3.23 (1H, d, J=6.9 Hz), 3.37(1H, dd, J=11.2 Hz), 3.45–3.61(1H, m), 4.76(1H, br s), 5.55(1H, dd, J=5.3, 12.2 Hz), 6.64(1H, d, J=8.3 Hz), 6.96(1H, br s), 7.23(1H, br s), 7.68–7.84(4H, m).

Example 3

Production of 2-(4-ethoxy-6-nitro-1,2,3,4-tetrahydroquinolin-2-yl)-2-methylpropan-1-ol

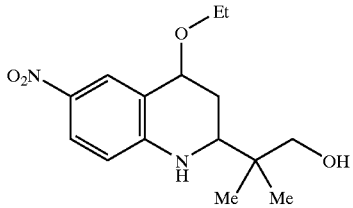

The compound of Example 1 (34 mg) was dissolved in 1.0 ml of tetrahydrofuran, and 1.2 ml of a 1M tetrahydrofuran solution of tetrabutylammonium fluoride was added at 0° C. After overnight stirring at room temperature, the solvent was distilled off under reduced pressure. The residue was purified by silica gel column chromatography (elution solvent; hexane:ethyl acetate=3:1–1:1–1:2) to obtain 14 mg of the title compound. Its physical properties are shown below.

¹H—NMR(CDCl₃) δ: 0.91(3H, s), 1.02(3H, s), 1.36(3H, t, J=7.3 Hz), 1.57(1H, q, J=11.9 Hz), 2.30(1H, br d, J=11.9 Hz), 3.51(1H, dd, J=3.0, 11.2 Hz), 3.58(1H, d, J=10.9 Hz), 3.65(1H, d, J=10.9 Hz), 3.63–3.71(1H, m), 3.77–3.88(1H, m), 4.53(1H, dd, J=5.3, 11.2 Hz), 6.26(1H, br s), 6.35(1H, d, J=8.9 Hz), 7.89(1H, d, J=8.9 Hz), 8.22(1H, br s).

Compounds shown in Examples 4 to 7 were produced in the same manner as in Example 3. The physical properties of the resulting compounds are shown in Table 1.

The compound of Example 35 (58 mg) was dissolved in 1.2 ml of pyridine, and 0.6 ml of acetic anhydride was added. After 2 hours of stirring at room temperature, the reaction mixture was diluted with ethyl acetate, and washed with distilled water. The organic layer was dried over anhydrous magnesium sulfate, and then the solvent was distilled off under reduced pressure. The residue was purified by silica gel column chromatography (elution solvent;

TABLE 1

| Ex. No. | X | R³ | ¹H-NMR δ: |
|---|---|---|---|
| 4 | —S— | —Et | (CDCl₃): 0.92(3H, s), 1.03(3H, s), 1.30(3H, t, J=7.3Hz), 1.80(1H, q, J=12.5Hz), 2.31(1H, ddd, J=2.6, 4.6, 12.5Hz), 2.49–2.69(2H, m), 3.48(1H, dd, J=2.6, 11.6Hz), 3.56(1H, d, J=10.8Hz), 3.69(1H, d, J=10.8Hz), 3.94(1H, dd, J=4.6, 12.5Hz), 6.38(1H, d, J=8.9Hz), 7.89(1H, dd, J=2.6, 8.9Hz), 8.52(1H, dd, J=1.3, 2.6Hz). |
| 5 | —S— | —Ph | (CDCl₃): 0.84(3H, s), 0.98(3H, s), 1.80(1H, q, J=12.2Hz), 2.29(1H, br d, J=12.2Hz), 3.44(1H, dd, J=2.6, 12.2Hz), 3.55(1H, d, J=10.9Hz), 3.63(1H, d, J=10.9Hz), 4.33(1H, dd, J=4.6, 12.2Hz), 6.37(1H, d, J=8.9Hz), 7.28–7.35(3H, m), 7.45(2H, dd, J=1.7, 7.9Hz), 7.90(1H, dd, J=2.6, 8.9Hz), 8.59(1H, br s). |
| 6 | —NH— | 4-NO₂-phenyl | (CDCl₃): 0.90(3H, s), 1.04(3H, s), 1.64(1H, q, J=11.9Hz), 2.09(1H, br s), 2.33(1H, br d, J=12.4Hz), 3.60(1H, d, J=10.9Hz), 3.66(1H, d, J=8.9Hz), 3.72(1H, d, J=10.9Hz), 4.73(1H, d, J=9.2Hz), 4.79–4.88(1H, m), 6.44(1H, d, J=9.2Hz), 6.51(1H, br s), 6.66(1H, d, J=9.2Hz), 7.91(1H, d, J=9.2Hz), 8.06(1H, s), 8.12(1H, d, J=9.2Hz). |
| 7 | —NHCO— | —H | (CDCl₃): 0.89(3H, s), 1.02(3H, s), 1.56(1H, q, J=11.9Hz), 2.23(1H, br d, J=11.9Hz), 3.56(1H, dd, J=2.6, 11.9Hz), 3.57(1H, d, J=10.9Hz), 3.67(1H, d, J=10.9Hz), 5.34(1H, ddd, J=5.0, 8.9, 11.9Hz), 6.10(1H, d, J=8.9Hz), 6.38(1H, d, J=8.9Hz), 6.51(1H, s), 7.86(1H, dd, J=2.6, 8.9Hz), 7.94(1H, br s), 8.43(1H, s). |

Example 8

Production of Acetic Acid 2-(4-dimethylamino-6-nitro-1,2,3,4-hexahydroquinolin-2-yl)-ethyl Ester

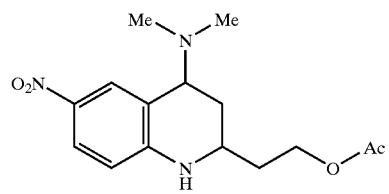

hexane:ethyl acetate=4:1) to obtain 51 mg of the title compound. Its physical properties are shown below.

¹H—NMR(CDCl₃) δ: 1.55(1H, q, J=11.9 Hz), 1.83–1.99 (2H, m), 2.07(1H, br d, J=11.9 Hz), 2.11(3H, s), 2.32(6H, s), 3.54–3.64(1H, m), 3.91(1H, dd, J=4.6, 11.9 Hz), 4.12–4.21 (1H, m), 4.35–4.44(1H, m), 4.82(1H, s), 6.39(1H, d, J=8.9 Hz), 7.92(1H, dd, J=2.6, 8.9 Hz), 8.40(1H, br s).

Compounds shown in Examples 9 to 14 were produced in the same manner as in Example 8. The physical properties of the resulting compounds are shown in Table 2.

TABLE 2

Structure: 6-nitro-4-(dimethylamino)-2-[2-methyl-2-(CH₂-Z-R⁴)propyl]-1,2,3,4-tetrahydroquinoline

| Ex. No. | Z | R⁴ | ¹H-NMR δ: |
|---|---|---|---|
| 9 | —OCO— | —Me | (CDCl$_3$): 1.02(3H, s), 1.05(3H, s), 1.56(1H, q, J=11.9Hz), 2.06(1H, br d, J=11.9Hz), 2.12(3H, s), 2.34(6H, s), 3.38(1H, dd, J=2.3, 11.9Hz), 3.86(1H, d, J=11.5Hz), 3.91(1H, dd, J=4.6, 11.9Hz), 4.18(1H, d, J=11.5Hz), 4.90(1H, s), 6.40(1H, d, J=8.9Hz), 7.91(1H, dd, J=3.0, 8.9Hz), 8.38(1H, br s). |
| 10 | —OCO— | —Ph | (CDCl$_3$): 1.14(3H, s), 1.16(3H, s), 1.63(1H, q, J=11.9Hz), 2.14–2.17(1H, m), 2.38(6H, s), 3.47(1H, dd, J=3.0, 11.9Hz), 4.00(1H, br d, J=11.9Hz), 4.14(1H, d, J=11.6Hz), 4.42(1H, d, J=11.6Hz), 4.97(1H, s), 6.40(1H, d, J=8.9Hz), 7.48(2H, t, J=7.3Hz), 7.62(1H, t, J=7.3Hz), 7.90(1H, dd, J=2.6, 8.9Hz), 8.04(2H, d, 7.3Hz), 8.44(1H, br s). |
| 11 | —OCO— | 4-fluorophenyl | (CDCl$_3$): 1.13(3H, s), 1.15(3H, s), 1.60(1H, q, J=11.9Hz), 2.12(1H, br d, J=11.9Hz), 2.34(6H, s), 3.45(1H, br d, J=11.9Hz), 3.92(1H, br d, J=11.9Hz), 4.13(1H, d, J=11.6Hz), 4.40(1H, d, J=11.6Hz), 4.88(1H, s), 6.40(1H, d, J=8.6Hz), 7.15(2H, t, J=8.3Hz), 7.91(1H, dd, J=2.3, 8.6Hz), 8.05(2H, dd, J=8.3Hz), 8.39(1H, br s). |
| 12 | —OCO— | 2,6-difluorophenyl | (CDCl$_3$): 1.13(6H, s), 1.58–1.63(1H, m), 2.10–2.20(1H, m), 2.43(6H, s), 3.49(1H, dd, J=3.3, 9.6Hz), 4.00–4.10(1H, m), 4.17(1H, d, J=11.5Hz), 4.43(1H, d, J=11.5Hz), 5.06(1H, s), 6.41(1H, d, J=9.2Hz), 7.02(2H, t, J=11.5Hz), 7.50(1H, tt, J=6.3, 8.3Hz), 7.91(1H, dd, J=2.6, 9.2Hz), 8.51(1H, br s). |
| 13 | —OSO$_2$— | —nPr | (CDCl$_3$): 1.09(6H, s), 1.10(3H, t, J=7.3Hz), 1.54(1H, q, J=11.9Hz), 1.87–1.96(2H, m), 2.07(1H, br d, J=11.9Hz), 2.36(6H, s), 3.12(2H, t, J=7.6Hz), 3.14(1H, br d, J=11.9Hz), 3.46(1H, dd, J=2.6, 11.9Hz), 4.06(1H, d, J=10.2Hz), 4.14(1H, d, J=10.2Hz), 4.77(1H, s), 6.46(1H, d, J=8.9Hz), 7.96(1H, dd, J=2.6, 8.9Hz), 8.40(1H, br s). |
| 14 | —O— | —CH$_2$OMe | (CDCl$_3$): 0.96(3H, s), 1.03(3H, s), 1.49(1H, q, J=11.9Hz), 2.01–2.05(1H, m), 3.35(6H, s), 3.39(3H, s), 3.41(1H, d, J=9.6Hz), 3.45(1H, dd, J=3.0, 11.9Hz), 3.52(1H, d, J=9.6Hz), 3.92(1H, dd, J=3.0, 11.9Hz), 4.64(1H, d, J=6.6Hz), 4.69(1H, d, J=6.6Hz), 5.88(1H, s), 6.34(1H, d, J=8.9Hz), 7.89(1H, dd, J=2.6, 8.9Hz), 8.38(1H, br s). |

Example 15

Production of 2-[2-(2-amino-1,1-dimethylethyl)-6-nitro-1,2,3,4-tetrahydroquinolin-4-yl]-isoindole-1,3-dione

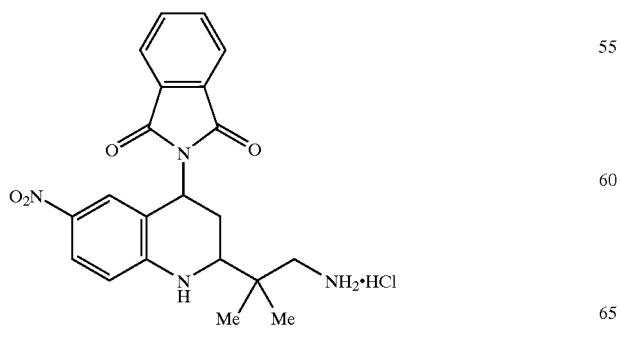

The compound of Example 2 (200 mg) was dissolved in 2 ml of tetrahydrofuran, and 2 ml of 2N hydrochloric acid was added. After overnight stirring at room temperature, the reaction mixture was filtered under reduced pressure. The resulting solid was dried in a vacuum to obtain 119 mg of the title compound. Its physical properties are shown below.

$^1$H—NMR(DMSO-d$_6$) δ: 1.05(3H, s), 1.07(3H, s), 2.12(1H, br s), 2.30(1H, q, J=11.9 Hz), 2.84–2.90(1H, m), 2.99–3.05(1H, m), 3.64(1H, d J=9.2 Hz), 5.49(1H, dd, J=5.0, 11.9 Hz), 7.70(1H, d, J=9.2 Hz), 7.14(1H, s), 7.58(1H, s), 7.83–7.93(4H, m), 7.98–8.06(3H, m).

Example 16

Production of N-{2-[4-(1,3-dioxo-1,3-dihydroisoindol-2-yl)-6-nitro-1,2,3,4-tetrahydroquinolin-2-yl]-2-methylpropyl}-isobutylamide

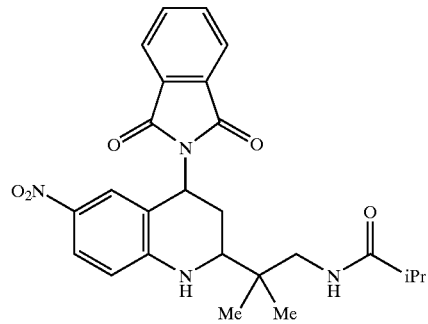

The compound of Example 15 (100 mg) was dissolved in 8 ml of dimethylformamide, and 0.2 ml of isobutyryl chloride and 0.2 ml of triethylamine were added. After overnight stirring at room temperature, distilled water was added, and the mixture was extracted with ethyl acetate. The organic layer was dried over anhydrous magnesium sulfate, and then the solvent was distilled off under reduced pressure. The residue was purified by silica gel column chromatography (elution solvent; hexane:ethyl acetate=1:1) to obtain 13 mg of the title compound. Its physical properties are shown below.

$^1$H—NMR(CDCl$_3$) δ: 0.84(3H, s), 0.90(3H, s), 1.65(1H, q, J=13.2 Hz), 2.04–2.08(1H, m), 2.16(3H, s), 2.17(3H, s), 2.32(3H, s), 3.08(1H, d, J=13.5 Hz), 4.01(1H, d, J=13.2 Hz), 5.10–5.20(1H, m), 6.72(1H, d, J=10.6 Hz), 6.88(1H, d, J=7.6 Hz), 6.92(1H, d, J=7.6 Hz), 7.16(1H, t, J=7.6 Hz), 7.21(1H, s), 7.77(1H, d, J=10.6 Hz), 7.89(1H, br s).

Compounds shown in Examples 17 to 21 were produced in the same manner as in Example 16. The physical properties of the resulting compounds are shown in Table 3.

TABLE 3

| Ex. No. | R$^1$ | Z | R$^4$ | $^1$H-NMR δ: |
|---|---|---|---|---|
| 17 | —NO$_2$ | —NHCO— | 4-Cl-C$_6$H$_4$— | (CDCl$_3$): 1.03(3H, s), 1.08(3H, s), 2.00(1H, br s), 2.66(1H, q, J=12.5Hz), 2.99(1H, dd, J=5.0, 14.5Hz), 3.41(1H, br d, J=9.2Hz), 4.01(1H, dd, J=8.6, 14.5Hz), 5.65(1H, dd, J=5.0, 12.5Hz), 6.14(1H, br s), 6.47–6.53(1H, m), 6.71(1H, d, J=9.2Hz), 7.40–7.46(2H, m), 7.62(1H, s), 7.67(1H, d, J=8.6Hz), 7.73–7.81(3H, m), 7.94(1H, dd, J=2.3, 8.9Hz), 8.02(1H, d, J=8.6Hz). |
| 18 | —NO$_2$ | —NHSO$_2$— | —Me | (CDCl$_3$): 1.01(3H, s), 1.04(3H, s), 2.00–2.10(1H, m), 2.60(1H, q, J=11.9Hz), 2.99(3H, m), 2.96–3.03(1H, m), 3.22(1H, dd, J=7.9, 13.5Hz), 3.61(1H, dd J=2.3, 11.9Hz), 5.12(1H, t, J=6.9Hz), 5.34(1H, br s), 5.59(1H, dd, J=4.6, 11.9Hz), 6.60(1H, d, J=9.2Hz), 7.64(1H, br s), 7.70–7.83(3H, m), 7.89(1H, dd, J=2.6, 9.2Hz), 7.85–7.95(1H, m). |
| 19 | —NO$_2$ | —NHSO$_2$— | 4-Cl-C$_6$H$_4$— | (CDCl$_3$): 0.91(3H, s), 0.98(3H, s), 2.06–2.09(1H, m), 2.25(1H, q, J=11.9Hz), 2.75(1H, dd, J=7.3, 13.3Hz), 2.92(1H, dd, J=7.3, 13.3Hz), 3.53(1H, d, J=9.6Hz), 5.46(1H, dd, J=5.0, 11.9Hz), 6.90(1H, d, J=9.2Hz), 6.92(1H, s), 7.58(1H, d, J=1.3Hz), 7.67(1H, dd, J=2.0, 6.6Hz), 7.69(1H, s), 7.78–7.97(7H, m), 8.01–8.05(1H, m). |
| 20 | —NO$_2$ | —NHSO$_2$— | 4-(MeC(O)NH)-C$_6$H$_4$— | (CDCl$_3$): 0.93(3H, s), 0.95(3H, s), 1.95–2.05(1H, m), 2.54(1H, q, J=11.7Hz), 2.70–2.80(1H, m), 2.89(3H, s), 2.97(3H, s), 2.90–3.10(2H, br s), 3.59(1H, d, J=10.2Hz), 5.54–5.86(1H, m), 5.86(1H, br s), 6.60(1H, d, J=8.9Hz), 7.62–7.66(2H, m), 7.74–8.02(9H, m), 8.43(1H, s). |

TABLE 3-continued

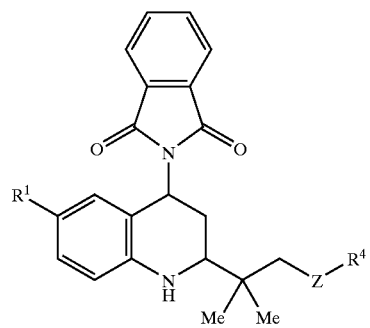

| Ex. No. | R¹ | Z | R⁴ | ¹H-NMR δ: |
|---|---|---|---|---|
| 21 | —CN | —NHCONH— | ![m-tolyl]  (3-Me-phenyl) | (CDCl₃): 0.91(3H, s), 0.92(3H, s), 1.93–1.98(1H, m), 2.24–2.30(1H, m), 2.30(3H, s), 2.62(1H, q, J=12.2Hz), 2.77(1H, d, J=14.5Hz), 3.37(1H, dd, J=2.0, 11.6Hz), 3.70(1H, br d, J=9.9Hz), 5.25(1H, br s), 6.62(1H, d, J=8.6Hz), 6.75(1H, br s), 6.91–6.93(2H, m), 7.06–7.12(2H, m), 7.19(2H, t, J=7.6Hz), 7.77–7.81(3H, m), 7.91(1H, br s). |

Example 22

Production of 2-(4-amino-6-nitro-1,2,3,4-tetrahydroquinolin-2-yl)-2-methylpropan-1-ol

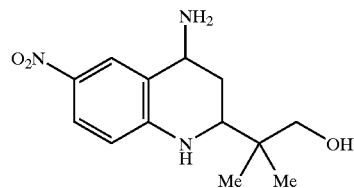

The compound of Example 7 (1.5 g) was dissolved in a mixed solution of 15 ml of tetrahydrofuran and 18 ml of methanol, and 15 ml of 6N hydrochloric acid was added. After 24 hours of stirring at room temperature, the reaction mixture was stirred for 2 hours at 70° C., followed by distilling off the solvent under reduced pressure. The residue was diluted with ethyl acetate, and a saturated aqueous solution of sodium hydrogen carbonate was added to neutralize the aqueous layer. The organic layer was dried over anhydrous magnesium sulfate, and the solvent was distilled off under reduced pressure. The residue was purified by silica gel column chromatography (elution solvent; ethyl acetate:methanol=2:1) to obtain 930 mg of the title compound. Its physical properties are shown below.

¹H—NMR(CDCl₃) δ: 0.84(3H, s), 0.91(3H, s), 1.51(1H, q, J=11.9 Hz), 2.19–2.26(1H, m), 3.45–3.50(2H, m), 4.36 (1H, dd, J=4.6, 11.9 Hz), 4.88(1H, br s), 6.83(1H, d, J=8.9 Hz), 6.99(1H, s), 7.84(1H, d, J=8.9 Hz), 8.22(1H, s).

Example 23

Production of 2-(4-dimethylamino-6-nitro-1,2,3,4-tetrahydroquinolin-2-yl)-2-methylpropan-1-ol

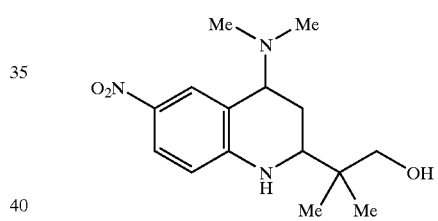

The compound of Example 22 (50 mg) was dissolved in 1.5 ml of methanol, and 0.04 ml of 35% formaldehyde, 120 mg of sodium triacetoxyborohydride, and 0.5 ml of acetic acid were added at 0° C., followed by stirring the mixture for 3 hours at room temperature. The solution was diluted with ethyl acetate, and the aqueous layer was neutralized with a saturated aqueous solution of sodium hydrogen carbonate. The organic layer was dried over anhydrous magnesium sulfate, and the solvent was distilled off under reduced pressure. The residue was purified by silica gel column chromatography (ethyl acetate) to obtain 44 mg of the title compound. Its physical properties are shown below.

¹H—NMR(CDCl₃) δ: 0.92(3H, s), 1.03(3H, s), 1.49(1H, q, J=11.9 Hz), 2.02(1H, br d, J=11.9 Hz), 2.34(6H, s), 3.46(1H, br d, J=11.9 Hz), 3.59(1H, d, J=10.9 Hz), 3.66(1H, d, J=10.9 Hz), 3.90(1H, dd, J=5.3, 11.9 Hz), 6.14(1H, s), 6.35(1H, d, J=8.9 Hz), 7.89(1H, dd, J=2.3, 8.9 Hz), 8.36(1H, br s).

Compounds shown in Examples 24 to 38 were produced in the same manner as in Example 23. The physical properties of the resulting compounds are shown in Tables 4, 5 and 6.

TABLE 4

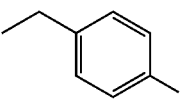

| Ex. No. | R³ | ¹H-NMR δ: |
|---|---|---|
| 24 | —nPr | (CDCl₃): 0.92(3H, s), 1.00(3H, t, J=7.3Hz), 1.02(3H, s), 1.41(1H, q, J=11.9Hz), 1.50–1.64(2H, m), 2.28(1H, br d, J=11.9Hz), 2.62(1H, ddd, J=6.3, 7.9, 10.9Hz), 2.79(1H, dt, J=10.9, 6.9Hz), 3.51(1H, dd, J=3.0, 11.9Hz), 3.58(1H, d, J=10.9Hz), 3.67(1H, d, J=10.6Hz), 3.86(1H, dd, J=4.6, 11.9Hz), 6.20(1H, s), 6.36(1H, d, J=8.9Hz), 7.90(1H, dd, J=2.6, 8.9Hz), 8.33(1H, br s). |
| 25 | —nBu | (CDCl₃): 0.92(3H, s), 0.95(3H, t, J=7.3Hz), 1.02(3H, s), 1.34–1.60(5H, m), 2.28(1H, br d, J=12.2Hz), 2.65(1H, dt, J=11.2, 6.9Hz), 2.83(1H, dt, J=11.2, 6.9Hz), 3.51(1H, dd, J=3.3, 11.6Hz), 3.58(1H, d, J=10.6Hz), 3.67(1H, dd, J=4.6, 10.6Hz), 3.86(1H, dd, J=4.3, 11.6Hz), 6.20(1H, s), 6.36(1H, d, J=8.9Hz), 7.90(1H, dd, J=2.3, 8.9Hz), 7.90(1H, dd, J=2.3, 8.9Hz), 8.32(1H, br s). |
| 26 | —(CH₂)₄—CH₃ | (CDCl₃): 0.91(3H, s), 1.01(3H, s), 1.36–1.47(7H, m), 2.27(1H, br d, J=Hz), 2.64(1H, dt, J=10.6, 6.9Hz), 2.82(1H, dt, J=10.6, 6.9Hz), 3.58(1H, d, J=10.6Hz), 3.66(1H, d, J=10.6Hz), 3.86(1H, dd, J=4.0, 11.2Hz), 6.21(1H, s), 6.36(1H, d, J=9.2Hz), 7.90(1H, dd, J=2.6, 9.2Hz), 8.38(1H, br s). |
| 27 | —(CH₂)₅—CH₃ | (CDCl₃): 0.88(3H, t, J=6.9Hz), 0.92(3H, s), 1.02(3H, s), 1.26–1.37(6H, m), 1.41(1H, q, J=11.9Hz), 1.51–1.61(2H, m), 2.27(1H, br d, J=11.9Hz), 2.65(1H, dt, J=10.9, 6.6Hz), 2.81(1H, dt, J=10.9. 6.6Hz), 3.51(1H, dd, J=4.0, 11.9Hz), 3.58(1H, d, J=10.9Hz), 3.66(1H, dd, J=4.6, 10.9Hz), 3.86(1H, dd, J=4.0, 11.9Hz), 6.21(1H, s), 6.36(1H, d, J=9.2Hz), 7.90(1H, dd, J=2.6, 9.2Hz), 8.32(1H, br s). |
| 28 | —iPr | (CDCl₃): 0.91(3H, s), 1.01(3H, s), 1.15(6H, t, J=6.3Hz), 1.31(1H, q, J=11.9Hz), 2.28(1H, br d, J=11.9Hz), 3.10–3.19(1H, m), 3.51(1H, dd, J=3.3, 11.9Hz), 3.58(1H, d, J=10.6Hz), 3.66(1H, d, J=10.6Hz), 3.85(1H, d, J=8.9Hz), 6.22(1H, s), 6.35(1H, d, J=8.9Hz), 7.88(1H, dd, J=2.6, 8.9Hz), 8.39(1H, br s). |
| 29 | —CH₂—tBu | (CDCl₃): 0.92(3H, s), 0.99(9H, s), 1.02(3H, s), 1.40(1H, q, J=11.9Hz), 2.25(1H, br d, J=11.9Hz), 2.33(1H, d, J=11.6Hz), 2.59(1H, d, J=11.6Hz), 3.51(1H, dd, J=3.0, 11.9Hz), 3.59(1H, d, J=10.6Hz), 3.67(1H, d, J=10.9Hz), 3.84(1H, dd, J=4.6, 11.9Hz), 6.17(1H, s), 6.35(1H, d, J=8.9Hz), 7.90(1H, dd, J=2.6, 8.9Hz), 8.43(1H, br s). |
| 30 | —Bn | (CDCl₃): 0.89(3H, s), 1.01(3H, s), 1.41(1H, q, J=11.9Hz), 2.34(1H, br d, J=11.9Hz), 3.47(1H, dd, J=3.0, 11.9Hz), 3.57(1H, d, J=10.9Hz), 3.65(1H, d, J=10.9Hz), 3.89(1H, d, J=13.2Hz), 4.03(1H, d, J=13.2Hz), 6.19(1H, s), 6.35(1H, d, J=8.9Hz), 7.26(1H, t, J=7.3Hz), 7.35(2H, t, J=7.3Hz), 7.45(2H, d, J=7.3Hz), 7.89(1H, dd, J=2.6, 8.9Hz), 8.47(1H, br s). |
| 31 | ![4-fluorobenzyl] | (CDCl₃): 0.85(3H, s), 0.96(3H, s), 1.35(1H, q, J=11.9Hz), 2.26(1H, br d, J=11.9Hz), 3.42(1H, dd, J=3.0, 11.9Hz), 3.52(1H, d, J=10.9Hz), 3.60(1H, d, J=10.9Hz), 3.79(1H, d, J=13.2Hz), 3.81(1H, dd, J=4.3, 11.9Hz), 3.93(1H, d, J=13.2Hz), 6.17(1H, s), 6.29(1H, d, J=8.9Hz), 6.98(2H, t, J=8.6Hz), 7.36(2H, dd, J=5.6, 8.6Hz), 7.83(1H, dd, J=2.6, 8.9Hz), 8.39(1H, br s). |

TABLE 5

| Ex. No. | R³=R⁷ | ¹H-NMR δ: |
|---|---|---|
| 32 | —Et | (CDCl₃): 0.91(3H, s), 1.02(3H, s), 1.10(6H, t, J=7.3Hz), 1.47(1H, q, J=11.9Hz), 2.00(1H, br d, J=11.9Hz), 2.38–2.50(2H, m), 2.54–2.67(2H, m), 3.45(1H, dd, J=2.6, 11.9Hz), 3.59(1H, d, J=10.9Hz), 3.66(1H, d, J=10.9Hz), 4.02(1H, dd, J=4.6, 11.9Hz), 6.13(1H, s), 6.34(1H, d, J=8.9Hz), 7.88(1H, dd, J=2.6, 8.9Hz), 8.44(1H, br s). |
| 33 | —nPr | (CDCl₃): 0.91(6H, t, J=7.3Hz), 0.92(3H, s), 1.03(3H, s), 1.43–1.58(5H, m), 2.02(1H, br d, J=11.9Hz), 2.42(4H, br s), 3.44(1H, dd, J=2.6, 11.2Hz), 3.59(1H, d, J=10.9Hz), 3.66(1H, d, J=10.9Hz), 3.96(1H, dd, J=4.3, 11.9Hz), 6.12(1H, s), 6.34(1H, d, J=8.9Hz), 7.88(1H, dd, J=2.6, 8.9Hz), 8.45(1H, br s). |

TABLE 5-continued

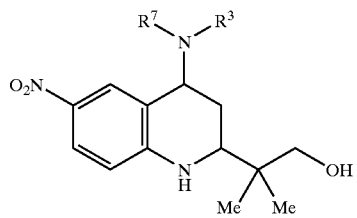

| Ex. No. | $R^3 = R^7$ | $^1$H-NMR δ: |
|---|---|---|
| 34 | —(CH$_2$)$_4$—CH$_3$ | (CDCl$_3$): 0.89(6H, t, J=6.9Hz), 0.92(3H, s), 1.02(3H, s), 1.20–1.40(8H, m), 1.43–1.55(5H, m), 2.01(1H, br d, J=11.2Hz), 2.43–2.46(4H, m), 3.44(1H, br d, J=11.2Hz), 3.59(1H, d, J=10.6Hz), 3.65(1H, d, J=10.6Hz), 3.97(1H, dd, J=4.0, 11.2Hz), 6.08(1H, s), 6.34(1H, d, J=8.9Hz), 7.88(1H, dd, J=2.6, 8.9Hz), 8.43(1H, br s). |

TABLE 6

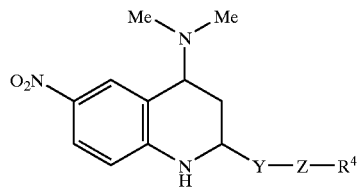

| Ex. No. | Y | Z | $R^4$ | $^1$H-NMR δ: |
|---|---|---|---|---|
| 35 | —(CH$_2$)$_2$— | —O— | —H | (CDCl$_3$): 1.56(1H, q, J=11.9Hz), 1.80–1.88(2H, m), 2.02(1H, br d, J=11.9Hz), 2.32(6H, s), 3.63–3.73(1H, m), 3.85–3.95(2H, m), 4.00–4.07(1H, m), 5.73(1H, s), 6.35(1H, d, J=8.9Hz), 7.90(1H, dd, J=2.6, 8.9Hz), 8.39(1H, br s). |
| 36 | —CH(CH$_3$)CH$_2$— | —O— | —H | (CDCl$_3$): 0.97(3H, d, J=7.3Hz), 1.52(1H, q, J=11.9Hz), 1.78–1.93(1H, m), 2.07(1H, br d, J=11.9Hz), 2.33(6H, s), 3.44(1H, ddd, J=3.3, 7.6, 11.9Hz), 3.69(1H, dd, J=8.9, 10.6Hz), 3.87(1H, dd, J=4.0, 10.6Hz), 3.89(1H, br d, J=11.9Hz), 5.99(1H, s), 6.34(1H, d, J=8.9Hz), 7.89(1H, dd, J=2.6, 8.9Hz), 8.38(1H, br s). |
| 37 | —C(CH$_3$)$_2$CH$_2$— | —O— | —Bn | (CDCl$_3$): 1.26(3H, s), 1.38(3H, s), 1.86–1.89(1H, m), 1.92–2.02(1H, m), 2.35(6H, s), 3.59(1H, t, J=6.3Hz), 3.65(1H, dd, J=3.6, 8.9Hz), 3.70(1H, t, J=6.3Hz), 3.95(1H, dd, J=4.0, 11.6Hz), 4.51(2H, s), 5.27(1H, br s), 6.36(1H, d, J=8.9Hz), 7.31–7.41(5H, m), 7.89(1H, dd, J=2.6, 8.9Hz), 8.38(1H, s). |
| 38 | —C(CH$_3$)$_2$CH$_2$— | —NHCONH— | ![3-methylphenyl]—Me | (CDCl$_3$): 0.84(3H, s), 0.90(3H, s), 1.65(1H, q, J=13.2Hz), 2.04–2.08(1H, m), 2.16(3H, s), 2.17(3H, s), 2.32(3H, s), 3.08(1H, d, J=13.5Hz), 4.01(1H, d, J=13.2Hz), 5.10–5.20(1H, m), 6.72(1H, d, J=10.6Hz), 6.88(1H, d, J=7.6Hz), 6.92(1H, d, J=7.6Hz), 7.16(1H, t, J=7.6Hz), 7.21(1H, s), 7.77(1H, d, J=10.6Hz), 7.89(1H, br s). |

Example 39

Production of N-[2-(2-hydroxy-1,1-dimethylethyl)-6-nitro-1,2,3,4-tetrahydroquinolin-4-yl]-propionamide

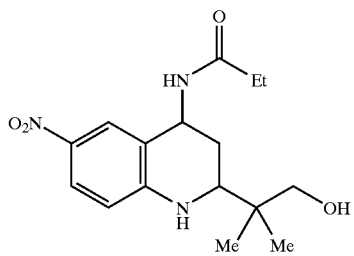

The compound of Example 22 (50 mg) and 0.1 ml of propionyl chloride were dissolved in 1 ml of pyridine. After 2 hours of stirring at room temperature, water and ethyl acetate were added. The ethyl acetate layer was washed with water, and then dried over anhydrous sodium sulfate, followed by distilling off the solvent under reduced pressure. The residue was dissolved in 1 ml of methanol, 0.1 ml of a 4N aqueous solution of sodium hydroxide was added, and the mixture was stirred for 1 hour. Then, a phosphate buffer (pH 7.0) was added, and the mixture was extracted with ethyl acetate. The organic layer was dried over anhydrous magnesium sulfate, and the solvent was distilled off under reduced pressure. The residue was purified by silica gel column chromatography (elution solvent: ethyl acetate) to obtain 31 mg of the title compound. Its physical properties are shown below.

$^1$H—NMR(CDCl$_3$) δ: 0.88(3H, s), 1.02(3H, s), 1.26(3H, d, J=7.6 Hz), 1.49(1H, q, J=11.9 Hz), 2.17–2.27(1H, m), 2.30–2.46(2H, m), 3.54–3.59(1H, m), 3.57(1H, d, J=10.9 Hz), 3.68(1H, d, J=10.9 Hz), 5.22–5.32(1H, m), 5.67(1H, d, J=8.9 Hz), 6.38(1H, d, J=8.9 Hz), 6.43(1H, s), 7.89(1H, dd, J=2.6, 8.9 Hz), 7.94(1H, s).

Compounds shown in Examples 40 to 41 were produced in the same manner as in Example 39. The physical properties of the resulting compounds are shown in Table 7.

Example 42

Production of 1-methyl-3-[2-(2-hydroxy-1,1-dimethylethyl)-6-nitro-1,2,3,4-tetrahydroquinolin-4-yl]-urea

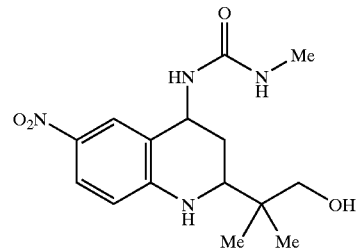

The compound of Example 22 (50 mg) and 30 mg of methyl thioisocyanate were dissolved in 1 ml of pyridine. After 2 hours of stirring at room temperature, the solvent was distilled off under reduced pressure. The residue was purified by silica gel column chromatography (elution solvent; hexane:ethyl acetate=1:2) to obtain 42 mg of the title compound. Its physical properties are shown below.

$^1$H—NMR(DMSO-d$_6$) δ: 0.85(3H, s), 0.92(3H, s), 1.17 (3H, t, J=6.6 Hz), 1.18(3H, t, J=6.9 Hz), 2.08(1H, br s), 3.52(1H, br d, J=9.2 Hz), 4.29(1H, br s), 4.89(1H, t, J=5.3 Hz), 5.62(1H, br s), 6.79(1H, d, J=9.2 Hz), 6.96(1H, s), 7.79(1H, s), 7.85(1H, dd, J=2.6, 9.2 Hz).

Compounds shown in Examples 43 to 45 were produced in the same manner as in Example 42. The physical properties of the resulting compounds are shown in Table 8.

TABLE 7

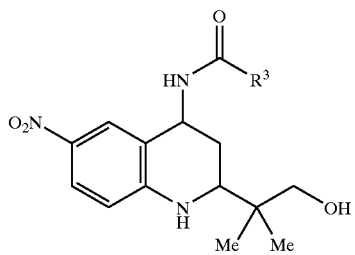

| Ex. No. | R$^3$ | $^1$H-NMR δ: |
|---|---|---|
| 40 | —iPr | (CDCl$_3$): 0.89(3H, s), 1.03(3H, s), 1.26(3H, d, J=6.9Hz), 1.31(3H, d, J= 6.9Hz), 1.49(1H, q, J=11.9Hz), 2.21(1H, br d, J=11.9Hz), 2.46–2.56(1H, m), 3.57(1H, dd, J=3.0, 10.2Hz), 3.68(1H, d, J=10.2Hz), 5.27–5.32(1H, m), 5.64(1H, d, J=8.6Hz), 6.38(1H, d, J=8.9Hz), 6.43(1H, s), 7.89(1H, dd, J=2.6, 8.9Hz), 8.43(1H, s). |
| 41 | —nBu | (CDCl$_3$): 0.87(3H, s), 0.98(3H, t, J=7.3Hz), 1.02(3H, s), 1.38–1.55(3H, m), 1.67–1.79(2H, m), 2.20(1H, br d, J=11.9Hz), 2.31–2.38(2H, m), 3.55(1H, dd, J=2.6, 11.9Hz), 3.56(1H, d, J=10.6Hz), 3.67(1H, d, J=10.6Hz), 5.25(1H, ddd, J=4.3, 9.2, 11.9Hz), 5.74(1H, d, J=2.3, 8.9Hz), 6.35(1H, d, J=8.9Hz), 6.43(1H, s), 7.85(1H, dd, J=2.3, 8.9Hz), 7.92(1H, br s). |

TABLE 8

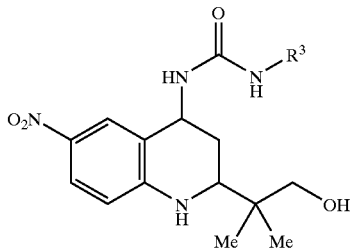

| Ex. No. | R³ | ¹H-NMR δ: |
|---|---|---|
| 43 | —nBu | (DMSO-d₆): 0.83(3H, s), 0.91(3H, t, J=6.6Hz), 0.91(3H, s), 1.25–1.49(5H, m), 1.99(1H, br s), 3.06–3.08(2H, m), 3.51(1H, br d, J=9.2Hz), 4.79–4.89(2H, m), 6.01(1H, t, J=5.6Hz), 6.24(1H, d, J=8.9Hz), 6.76(1H, d, J=9.9Hz), 6.91(1H, s), 7.84(2H, br s). |
| 44 | —iPr | (DMSO-d₆): 0.83(3H, s), 0.91(3H, s), 1.08(3H, d, J=6.6Hz), 1.11(3H, d, J= 6.6Hz), 1.41(1H, q, J=11.5Hz), 2.01(1H, br d, J=11.5Hz), 3.51(1H, br d, J= 11.5Hz), 3.72–3.79(1H, m), 4.79–4.87(2H, m), 5.86(1H, d, J=7.9Hz), 6.13(1H, d, J=8.9Hz), 6.75(1H, d, J=9.6Hz), 6.90(1H, s), 7.81–7.84(2H, m). |
| 45 | —tBu | (DMSO-d₆): 0.83(3H, s), 0.91(3H, s), 0.91(9H, s), 2.02(1H, br s), 3.51(1H, br d, J=9.2Hz), 4.70–4.80(1H, m), 4.86(1H, t, J=5.0Hz), 5.82(1H, s), 6.05(1H, d, J=8.9Hz), 6.75(1H, d, J=8.6Hz), 6.89(1H, s), 7.83(1H, d, J=8.6Hz), 7.84(1H, s). |

Examples 46, 47

Production of 2-(4-ethanesulfonyl-6-nitro-1,2,3,4-tetrahydroquinolin-2-yl)-2-methylpropan-1-ol and 2-(4-ethanesulfinyl-6-nitro-1,2,3,4-tetrahydroquinolin-2-yl)-2-methylpropan-1-ol

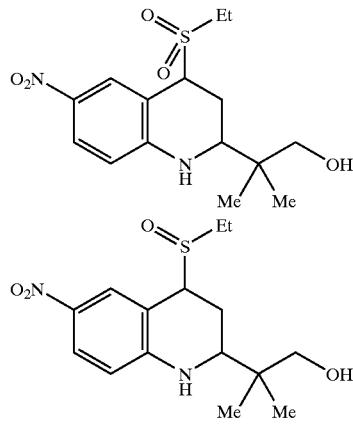

The compound of Example 4 (55 mg) was dissolved in 1 ml of dichloromethane, and 40 mg of m-chloroperbenzoic acid was added under cooling with ice. After 10 minutes of stirring, a saturated aqueous solution of sodium hydrogen carbonate and ethyl acetate were added, and the mixture was extracted with an ethyl acetate layer. The organic layer was dried over anhydrous magnesium sulfate, and the solvent was distilled off under reduced pressure. The residue was purified by silica gel column chromatography (elution solvents; hexane:ethyl acetate=4:1–ethyl acetate:ethanol=10:1) to obtain 13 mg of the compound of Example 46 and 15 mg of the compound of Example 47. Their physical properties are shown below.

Example 46: ¹H—NMR(CDCl₃) δ: 0.93(3H, s), 1.09(3H, s), 1.36(3H, t, J=7.3 Hz), 1.95(1H, q, J=11.5 Hz), 2.61(1H, ddd, J=2.3, 6.6, 11.5 Hz), 2.76–2.93(2H, m), 3.31(1H, dd, J=2.3, 11.5 Hz), 3.60(1H, d, J=10.6 Hz), 3.70(1H, d, 10.6 Hz), 4.42(1H, dd, J=6.6, 11.5 Hz), 6.43(1H, s), 6.54(1H, d, J=8.9 Hz), 7.79(1H, dd, J=2.6, 8.9 Hz), 8.78(1H, d, J=2.6 Hz).

Example 47: ¹H—NMR(CDCl₃) δ: 0.93(3H, s), 1.09(3H, s), 1.35(3H, t, J=7.6 Hz), 1.82(1H, q, J=11.9 Hz), 2.33–2.82 (3H, m), 3.37(1H, dd, J=2.3, 11.9 Hz), 3.59–3.73(2H, m), 4.40–4.60(1H, m), 6.49(1×1/2H, d, J=8.9 Hz), 6.51(1×1/2H, d, J=8.9 Hz), 7.95(1H, dd, J=2.6, 8.9 Hz), 8.10(1×1/2H, d, J=2.0 Hz), 8.32(1×1/2H, d, J=2.0 Hz).

The following compounds are named as concrete examples of the compounds of the present invention. They can be produced by the same methods as in the foregoing Examples:

First Group (R¹ = CN, R² = H, X = —NR⁷—)

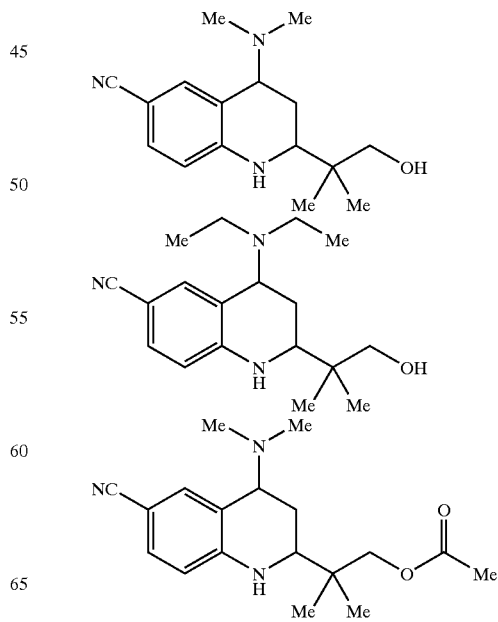

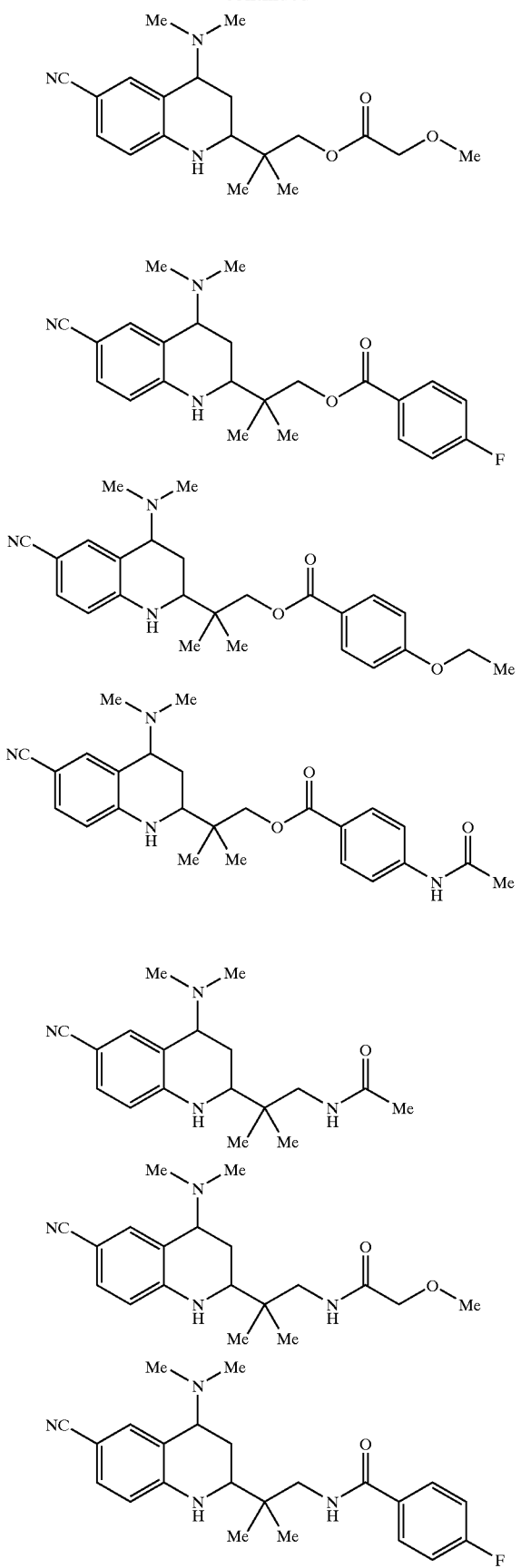
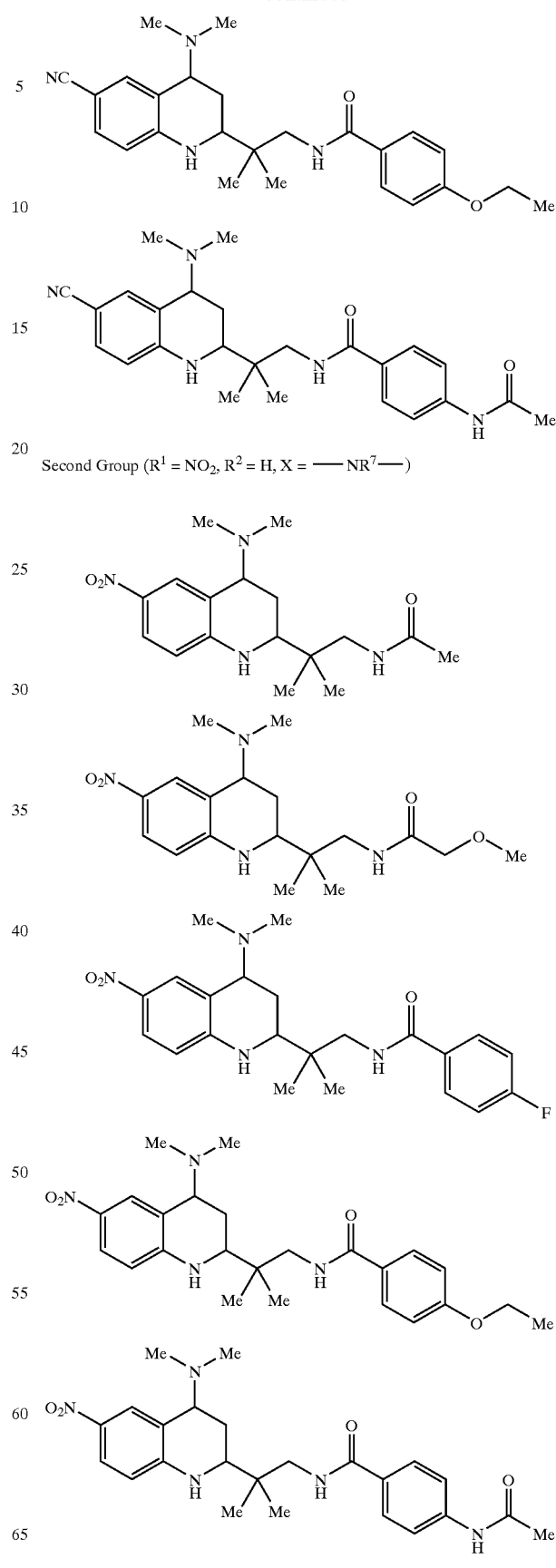
Second Group ($R^1 = NO_2$, $R^2 = H$, $X = -NR^7-$)

-continued
Third Group (R1 = CN, R2 = H, X = —O—)
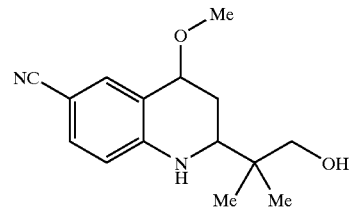
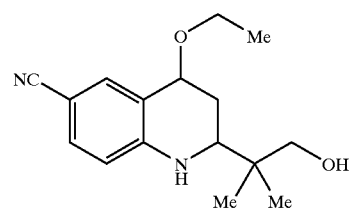
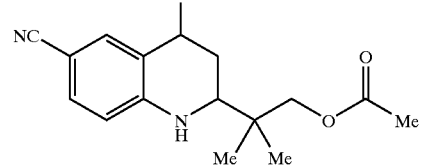
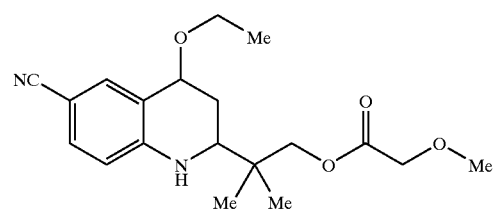
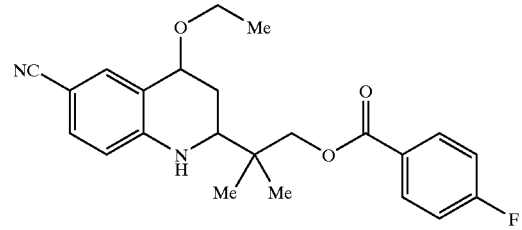
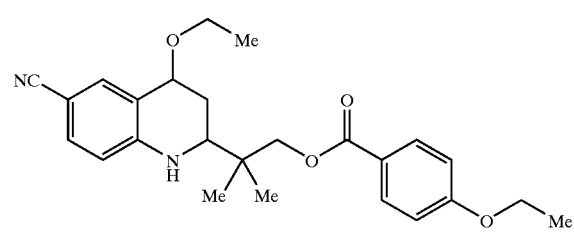
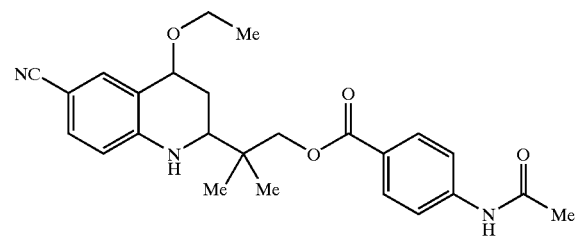
-continued
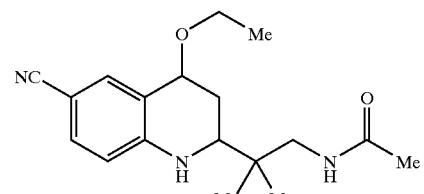
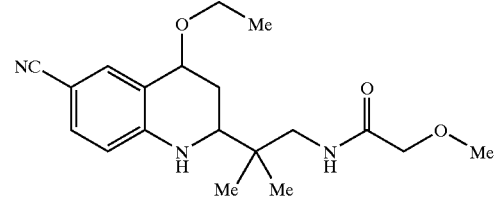
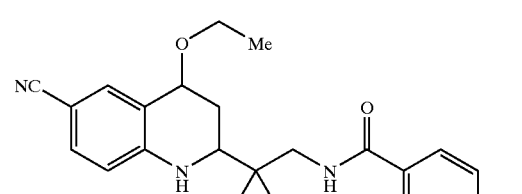
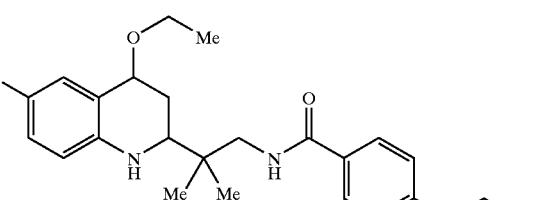
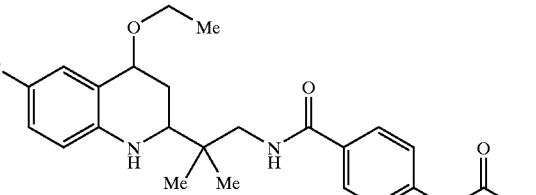
Fourth Group (R$^1$ = NO$_2$, R$^2$ = H, X = —O—)
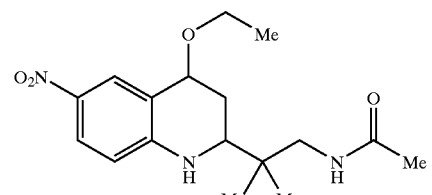
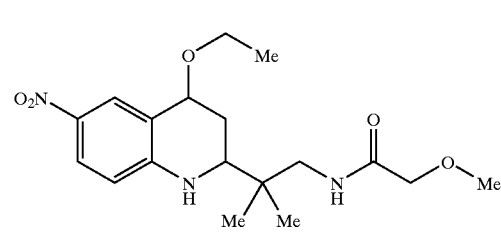

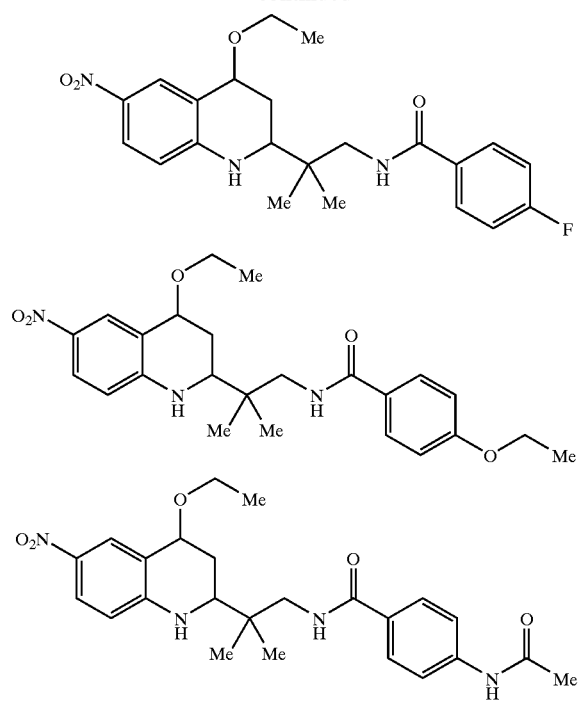
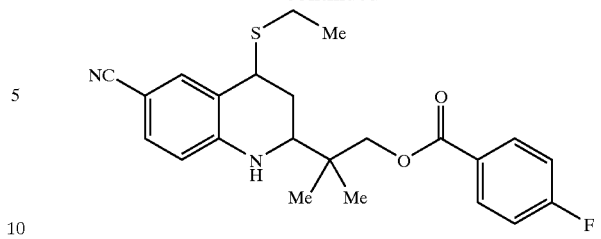
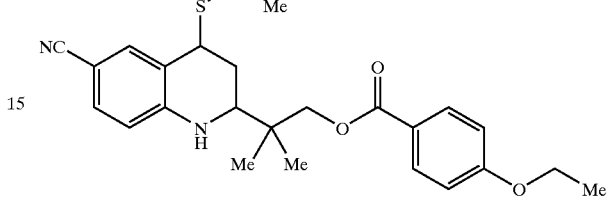
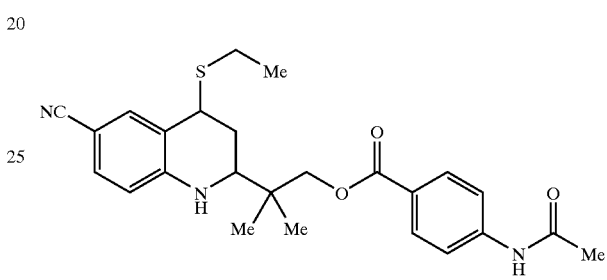
Fifth Group (R¹ = CN, R² = H, X = —S—)
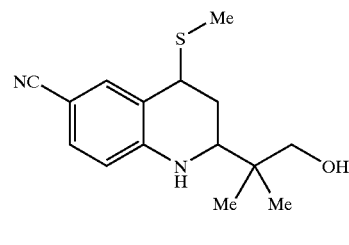
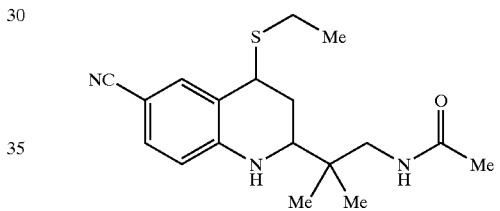
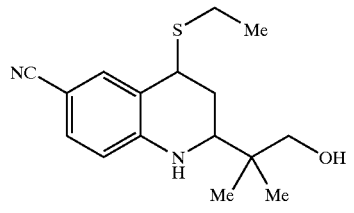
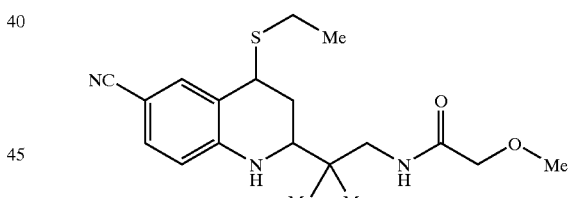
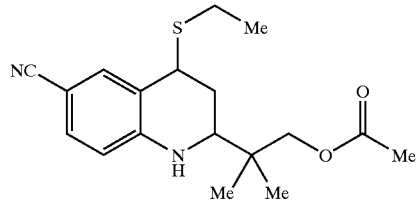
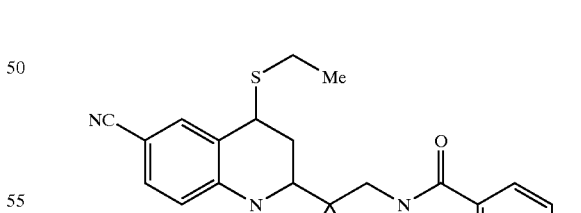
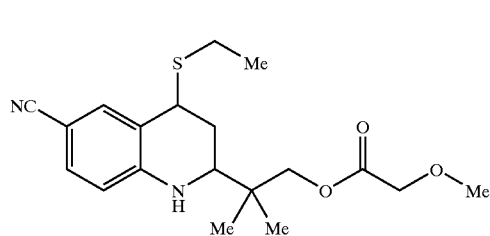
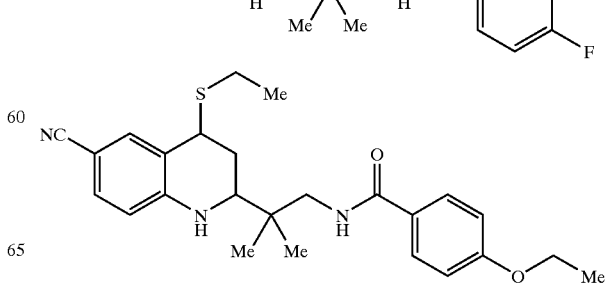

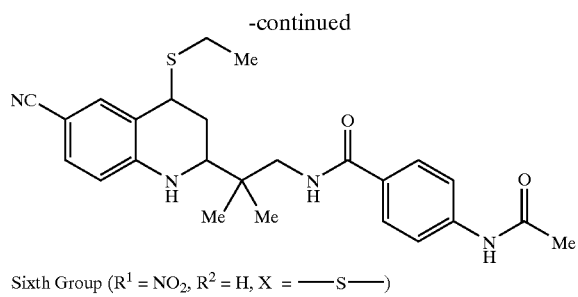

Sixth Group ($R^1 = NO_2$, $R^2 = H$, $X = \text{---S---}$)

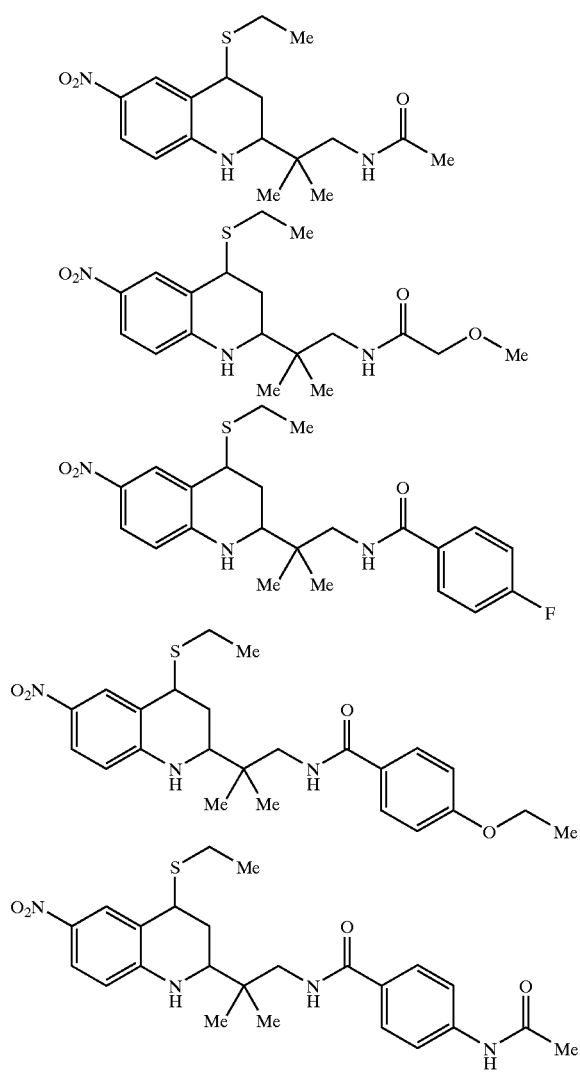

Next, the usefulness of the compounds of the present invention will be described by the following test examples:

Test Example 1

Test for Competitive Binding to Rat Androgen Receptors (Rat AR)

Preparation of rat AR fraction: Prostates were harvested into ice-cooled ET buffer (10 mM Tris, 1 mM EDTA, 5 mM DTT, 10 mM sodium molybdate, pH 7.4) 3 days after orchiectomy in 11-week-old male SD rats. The prostate was finely cut, and ET buffer was added, whereafter the mixture was homogenized using a homogenizer. The homogenate was ultracentrifuged (100,000×g, 60 min, 4° C.), and the supernatant was used as a rat AR fraction (hereinafter referred to as ARF).

Binding test: $^3$H-testosterone (hereinafter referred to as $^3$H-T) was diluted with ET buffer. Dihydrotestosterone (DHT) was prepared so as to have a concentration (final concentration 1 μM) 400 times the maximum concentration of $^3$H-T (2.5 nM). The $^3$H-T solution was added to a 1.5 ml tube containing DHT, no DHT, or the test compound with a varying concentration. Further, 200 μg ARF was added to adjust the final volume to 100 μl. The mixture was incubated for 2 hours at 4° C., and then 300 μl of a 0.05% dextran T70–1.0% activated carbon solution was added. The mixture was further incubated for 15 minutes in ice to remove the free $^3$H-T. After centrifugation (4° C., 2,500 rpm, 5 min), 275 μl of the supernatant was harvested into a liquid scintillation vial, and 2 ml of clear-sol was added. The mixture was stirred, allowed to stand, and measured for $^3$H radioactivity with a liquid scintillation counter.

Calculation of the relative binding inhibition rate: The binding inhibition rate (%) of the compound according to the present invention was calculated from the following equation, and the 50% inhibition concentration ($IC_{50}$) was calculated by the probit analysis of the concentration-binding inhibition curve.

Binding inhibition rate (%)=100×[1−(a−c)/(b−c)] where a: Radioactivity of the sample incorporating the compound of the present invention ($^3$H-T+compound)
b: Radioactivity of the sample free from the compound of the present invention (only $^3$H-T: amount of total binding)
c: Radioactivity of the sample incorporating DHT ($^3$H-T+DHT: amount of nonspecific binding)

The relative binding inhibition rate (RBA: Relative Binding Affinity) was obtained from the following equation (Endocrinology 138, 863–870, 1997):

RBA=100×($IC_{50}$ of hydroxyflutamide)/($IC_{50}$ of the compound of the present invention)

RBA's of the compounds of the present invention, calculated as above, are shown in Table 9.

TABLE 9

| Test Compounds | RBA |
|---|---|
| Example 3 | 958 |
| Example 4 | 2355 |
| Example 5 | 480 |
| Example 9 | 79 |
| Example 11 | 98 |
| Example 23 | 710 |
| Example 30 | 370 |
| Example 33 | 423 |
| Hydroxyflutamide | 100 |

The RBA's determined, with the binding inhibition rate of hydroxyflutamide taken as 100, showed the compounds of the present invention to have very strong binding inhibition activity.

Test Example 2

Action of Increasing Prostate Weight in Orchiectomized (ORX) Rats

Testes were removed from 8-week-old male SD rats. From 5 days after the operation, the positive control compound dihydrotestosterone (DHT, 10 mg/kg) or the compound of the present invention (Example 23, 30 mg/kg), dissolved in a 5% dimethyl sulfoxide-containing olive oil solution, was subcutaneously administered once daily for 8 days. In an ORX control group (Vehicle), dimethyl sulfoxide diluted with olive oil was used for the test. The rats, which had been falsely operated on without orchiectomy, were used as a normal control group (Sham). On the next day after final administration, the wet weight of the ventral prostate was measured to evaluate the AR agonistic effect of the compound of the present invention. The results are shown in Table 10.

TABLE 10

|  | Weight of prostate mg/body weight (100 g) |
| --- | --- |
| Normal control (Sham) | 93 ± 11 |
| ORX Control (Vehicle) | 10 ± 2++ |
| DHT 10 mg/kg | 68 ± 16** |
| Ex. 23 30 mg/kg | 52 ± 12** |

Mean ± SD
**$p < 0.01$ on Dunnett's t-test (vs Vehicle)
++$p < 0.01$ on unpaired t-test (vs Sham)

The compound of Example 23, when consecutively administered for 8 days, significantly increased prostate weights in comparison with the ORX control. Furthermore, this compound restored the atrophied prostate up to a level comparable to the level of DHT, a natural androgen, demonstrating excellent AR agonistic action.

Test Example 3

Action of Increasing Prostate Weight and Bone Mass in Orchiectomized (ORX) Rats

Orchiectomy was performed in 12-week-old male SD rats. From the next day after operation, the positive control compound dihydrotestosterone (DHT, 10 mg/kg) and the compound of the present invention (Example 23, 30 mg/kg), each dissolved in a 5% dimethyl sulfoxide-containing olive oil solution, were subcutaneously administered once daily, 5 days weekly, for 4 weeks. In an ORX control group (Vehicle), dimethyl sulfoxide diluted with olive oil was used for the test. The rats, which had been falsely operated on without orchiectomy, were used as a normal control group (Sham). On the next day after final administration, the wet weight of the ventral prostate was measured to evaluate the AR agonistic effect of the compound of the present invention. On the next day following final administration, moreover, the right femur was removed, and fixed overnight in a 10% neutrally buffered formalin solution. Then, the bone mineral density at the site ranging from the diaphysis to the proximal end was measured by the method of double energy X-ray absorption using a bone mineral content-measuring machine (Aloka, DCS-600) to evaluate the action of increasing bone mass of the compound of the present invention. The results are shown in Table 11.

TABLE 11

|  | Prostate weight (mg/body weight 100 g) | Bone mineral density (mg/cm$^2$) |
| --- | --- | --- |
| Normal control (Sham) | 97 ± 13 | 136 ± 7 |
| ORX Control (Vehicle) | 9 ± 2++ | 125 ± 5++ |

TABLE 11-continued

|  | Prostate weight (mg/body weight 100 g) | Bone mineral density (mg/cm$^2$) |
| --- | --- | --- |
| DHT 10 mg/kg | 150 ± 14** | 130 ± 7 |
| Ex. 23 30 mg/kg | 78 ± 10** | 134 ± 6** |

Mean ± SD
**$p < 0.01$ on Dunnett's t-test (vs Vehicle).
++$p < 0.01$ on unpaired t-test (vs Sham).

The compound of Example 23, when administered for 4 weeks, restored the atrophied prostate up to the level of the normal control. Also, this compound significantly increased the decreased bone mineral density in comparison with the control group. Thus, this compound showed excellent AR agonistic activity.

Test Example 4

Action of Increasing Bone Mass in Ovariectomized (OVX) Rats

Ovariectomy was performed in 12-week-old female SD rats. From 4 weeks postoperatively, the positive control compound dihydrotestosterone (DHT, 10 mg/kg) and the compound of the present invention (Example 23, 30 mg/kg), each dissolved in a 10% dimethyl sulfoxide-containing olive oil solution, were subcutaneously administered once daily, 5 days weekly, for 8 weeks. In an OVX control group (Vehicle), dimethyl sulfoxide diluted with olive oil was used for the test. The rats, which had been falsely operated on without ovariectomy, were used as a normal control group (Sham). On the next day after final administration, the right femur was removed, and fixed overnight in a 10% neutrally buffered formalin solution. Then, the bone mineral density at the site ranging from the diaphysis to the proximal end was measured by the method of double energy X-ray absorption using a bone mineral content-measuring machine (Aloka, DCS-600) to evaluate the action of increasing bone mass of the compound of the present invention. The results are shown in Table 12.

TABLE 12

|  | Bone mineral density (mg/cm$^2$) |
| --- | --- |
| Normal control (Sham) | 118.3 ± 3.3 |
| OVX Control (Vehicle) | 115.3 ± 3.3 |
| DHT 10 mg/kg | 120.8 ± 4.4** |
| Ex. 23 30 mg/kg | 120.9 ± 3.9** |

Mean ± SD
*$p < 0.05$,
**$p < 0.01$ on Dunnett's t-test (vs Vehicle).

The compound of Example 23, when administered for 8 weeks, significantly increased the bone mineral density decreased in 4 postoperative weeks. Thus, this compound showed excellent AR agonistic activity even in postmenopausal osteoporosis model animals.

Test Example 5

AR Antagonistic Effect

Testes were removed from male rats. From 5 days postoperatively, testosterone propionate and the compound of the present invention were simultaneously administered once daily for one consecutive week by the subcutaneous route. On the next day after final administration, the wet weight of the ventral prostate was measured to evaluate the AR antagonistic effect of the compound of the present invention based on its inhibitory action on testosterone propionate-induced prostate weight increase.

Preparation examples of the compound of the present invention will be shown below, but formulations of the compound are not restricted to them.

Preparation Example 1

Tablets

In accordance with the following formulation, tablets containing 2 mg of an active ingredient per tablet were prepared:

| | |
|---|---|
| Compound of Example 23 | 2 mg |
| Starch | 48 mg |
| Lactose | 30 mg |
| Cellulose, microcrystalline | 15 mg |
| Methyl cellulose | 3 mg |
| Magnesium stearate | 2 mg |
| Total amount | 100 mg |

Preparation Example 2

Capsules

In accordance with the following formulation, 100 mg of an ingredient mixture containing 2 mg of an active ingredient per capsule were encapsulated to prepare capsules:

| | |
|---|---|
| Compound of Example 23 | 2 mg |
| Starch | 38 mg |
| Lactose | 50 mg |
| Cellulose, microcrystalline | 8 mg |
| Magnesium stearate | 2 mg |
| Total | 100 mg |

INDUSTRIAL APPLICABILITY

The tetrahydroquinoline compounds of the present invention, and pharmaceuticals containing them as active ingredients have a specific and strong binding affinity for AR, and have an AR agonistic or antagonistic action. Thus, they can specifically modulate the function of AR, and can prevent and treat various AR-related diseases. As AR agonists, particularly, they do not excessively act on the prostate, but show potent action on skeletal muscle tissue and bone tissue. Hence, the compounds of the present invention can be used in the prevention or treatment of hypogonadism as pharmaceuticals with moderate action on the prostate and with less adverse effects. In the prophylaxis or treatment of wasting diseases and osteoporosis, they can be expected to show potent activity on target tissues, such as skeletal muscle tissue and bone tissue.

What is claimed is:

1. A tetrahydroquinoline compound represented by the following formula (I) or pharmacologically acceptable salts thereof:

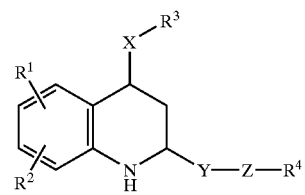

wherein $R^1$ and $R^2$ each independently represent a hydrogen atom, an alkyl group having 1–9 carbon atoms, an alkoxy group having 1–9 carbon atoms, a halogen atom, a nitro group, —$NR^5R^6$ (wherein $R^5$ and $R^6$ each independently represent a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom and a nitro group, an aryl, furyl or pyridyl group which may optionally be substituted by one or more members selected from the group consisting of an alkyl group having 1–9 carbon atoms, an alkoxy group having 1–9 carbon atoms, a halogen atom and a nitro group, a formyl group, an aliphatic acyl group having 2–5 carbon atoms, an aliphatic acyloxy group having 2–5 carbon atoms, an aromatic acyl group, an alkylsulfonyl group having 1–4 carbon atoms, an arylsulfonyl group, an alkoxycarbonyl group having 2–5 carbon atoms, a hydroxyoxalyl group, or an alkoxyoxalyl group having 3–7 carbon atoms), a carboxyl group, an alkoxycarbonyl group having 2–5 carbon atoms, an amido group, an alkylamido group having 2–5 carbon atoms, an alkylthio group having 1–4 carbon atoms, an alkylsulfinyl group having 1–4 carbon atoms, an alkylsulfonyl group having 1–4 carbon atoms, a cyano group, a sulfamoyl group, an alkylsulfamoyl group having 1–4 carbon atoms, an amidino group, or an alkyl or alkoxy group having 1–5 carbon atoms which has been substituted by fluorine atom(s);

X represents —O—, —OCO—, —OSO$_2$—, —S—, —SCO—, —SO—, —SO$_2$—, —NR$^{7'}$—, —NR$^7$CO—, —NR$^7$SO$_2$—, —NR$^7$CONH—, —NR$^7$CSNH— or —NR$^7$COCO— (wherein R$^{7'}$ represents an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxyalkyl group having 2–5 carbon atoms, or an aryl, furyl or pyridyl group which may optionally be substituted by one or more members selected from the group consisting of an alkyl group having 1–9 carbon atoms, an alkoxy group having 1–9 carbon atoms, a halogen atom, and a nitro group and R$^7$ represents a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxyalkyl group having 2–5 carbon atoms, or an aryl, furyl or pyridyl group which may optionally be substituted by one or more members selected from the group consisting of an alkyl group having 1–9 carbon atoms, an alkoxy group having 1–9 carbon atoms, a halogen atom, and a nitro group);

$R^3$ represents a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxyalkyl group having 2–5 carbon atoms, or an aryl, furyl or pyridyl group which may optionally be substituted by $R^8$ (wherein $R^8$ represents an alkyl group having 1–9 carbon atoms, an alkoxy group having 1–9 carbon atoms, a halogen atom or a nitro group), provided that when X is $NR^7$, $R^3$ and $R^7$ may, together with the nitrogen atom to which they are bonded, form a 3- to 6-membered cyclic amino group or a 4- to 10-membered cyclic imido group;

Y represents an alkylene group having 1–9 carbon atoms which may optionally be substituted by alkyl group(s) having 1–9 carbon atoms, cycloalkyl group(s) having 3–7 carbon atoms, hydroxylgroup(s), alkoxy group(s) having 1–9 carbon atoms or —$NR^9R^{10}$ (wherein $R^9$ and $R^{10}$ each independently have the same meaning as $R^5$);

Z represents a single bond, —O—, —OCO—, —$OSO_2$—, —S—, —SCO—, —SO—, —$SO_2$—, —$NR^{11}$—, —$NR^{11}CO$—, —$NR^{11}SO_2$—, —$NR^{11}CONH$—, —$NR^{11}CSNH$—, —$NR^{11}COO$— or —$NR^{11}COCO$— (wherein $R^{11}$ represents a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxyalkyl group having 2–5 carbon atoms, or an aryl, furyl or pyridyl group which may optionally be substituted by $R^{12}$ (wherein $R^{12}$ is an alkyl group having 1–9 carbon atoms, an alkoxy group having 1–9 carbon atoms, a halogen atom, a nitro group, an aryl, furyl or pyridyl group which may optionally be substituted by one or more members selected from the group consisting of an alkyl group having 1–9 carbon atoms, an alkoxy group having 1–9 carbon atoms, a halogen atom, and a nitro group, —$NR^{13}R^{14}$ (wherein $R^{13}$ and $R^{14}$ each independently have the same meaning as $R^5$), a carboxyl group, an alkoxycarbonyl group having 2–5 carbon atoms, an amido group, an alkylamido group having 2–5 carbon atoms, an alkylthio group having 1–4 carbon atoms, an alkylsulfinyl group having 1–4 carbon atoms, an alkylsulfonyl group having 1–4 carbon atoms, a cyano group, a sulfamoyl group, an alkylsulfamoyl group having 1–4 carbon atoms, or an alkyl or alkoxy group having 1–5 carbon atoms which has been substituted by fluorine atom(s))); and $R^4$ represents a hydrogen atom, an alkyl group having 1–9 carbon atoms, a cycloalkyl group having 3–7 carbon atoms, an aralkyl group having 7–9 carbon atoms which may optionally be substituted by one or more members selected from the group consisting of an alkyl group having 1–9 carbon atoms, an alkoxy group having 1–9 carbon atoms, a halogen atom, and a nitro group, an alkoxy group having 1–9 carbon atoms, an alkoxyalkyl group having 2–5 carbon atoms, a halogen atom, a silyl group substituted by hydrocarbon group(s), or an aryl, furyl or pyridyl group which may optionally be substituted by $R^{15}$ (wherein $R^{15}$ independently has the same meaning as $R^{12}$), provided that when Z is other than a single bond, $R^4$ is not a halogen atom.

2. The tetrahydroquinoline compound or pharmacologically acceptable salts thereof according to claim 1, wherein $R^1$ is a nitro group or a cyano group;

$R^2$ is a hydrogen atom;

X is —O—, —S—, —SO—, —$SO_2$—, —$NR^{7\prime}$—, —$NR^7CO$—, —$NR^7SO_2$—, —$NR^7CONH$—, or —$NR^7CSNH$— (wherein $R^{7\prime}$ is an alkyl group having 1–9 carbon atoms, an aralkyl group having 7–9 carbon atoms, an aryl, furyl or pyridyl group and $R^7$ is a hydrogen atom, an alkyl group having 1–9 carbon atoms, an aralkyl group having 7–9 carbon atoms, an aryl, furyl or pyridyl group);

$R^3$ is a hydrogen atom, an alkyl group having 1–9 carbon atoms, an aralkyl group having 7–9 carbon atoms, or an aryl, furyl or pyridyl group which may optionally be substituted by $R^8$ (wherein $R^8$ is an alkyl group having 1–9 carbon atoms, an alkoxy group having 1–9 carbon atoms, a halogen atom or a nitro group), provided that when X is $NR^7$, $R^3$ and $R^7$ may, together with the nitrogen atom to which they are bonded, form a 3- to 6-membered cyclic amino group or a 4- to 10-membered cyclic imido group;

Y is an alkylene group having 1–9 carbon atoms which may optionally be substituted by alkyl group(s) having 1–9 carbon atoms;

Z is —O—, —OCO—, —$OSO_2$—, —NH—, —NHCO—, —$NHSO_2$—, —NHCONH—, —NHCSNH—, or —NHCOO—;

$R^4$ is a hydrogen atom, an alkyl group having 1–9 carbon atoms, an aralkyl group having 7–9 carbon atoms, an alkoxyalkyl group having 2–5 carbon atoms, a silyl group substituted by hydrocarbon group(s), or an aryl, furyl, or pyridyl group which may optionally be substituted by $R^{15}$ (wherein $R^{15}$ is an alkyl group having 1–9 carbon atoms, an alkoxy group having 1–9 carbon atoms, a halogen atom, or an acetamido group).

3. A pharmaceutical composition comprising the tetrahydroquinoline compound or pharmacologically acceptable salts thereof according to claim 1 or 2 as an active ingredient and a pharmaceutically acceptable carrier.

* * * * *